United States Patent
Li et al.

(10) Patent No.: US 11,478,594 B2
(45) Date of Patent: Oct. 25, 2022

(54) SYSTEMS AND METHODS FOR RESPIRATORY EFFORT DETECTION UTILIZING SIGNAL DISTORTION

(71) Applicant: Covidien LP, Mansfield, MA (US)

(72) Inventors: Kun Li, San Diego, CA (US); Fengdan Dong, San Marcos, CA (US); Gabriel Sanchez, Valley Center, CA (US)

(73) Assignee: Covidien LP, Mansfield, MA (US)

( * ) Notice: Subject to any disclaimer, the term of this patent is extended or adjusted under 35 U.S.C. 154(b) by 512 days.

(21) Appl. No.: 16/411,916

(22) Filed: May 14, 2019

(65) Prior Publication Data

US 2019/0344034 A1   Nov. 14, 2019

Related U.S. Application Data

(60) Provisional application No. 62/740,740, filed on Oct. 3, 2018, provisional application No. 62/671,063, filed on May 14, 2018.

(51) Int. Cl.
*A61M 16/00* (2006.01)
*A61M 16/20* (2006.01)
*G16H 20/40* (2018.01)

(52) U.S. Cl.
CPC ...... *A61M 16/022* (2017.08); *A61M 16/0003* (2014.02); *A61M 16/204* (2014.02); *A61M 2016/0015* (2013.01); *A61M 2016/0039* (2013.01); *A61M 2016/0042* (2013.01); *G16H 20/40* (2018.01)

(58) Field of Classification Search
CPC . A61M 16/022; A61M 16/026; A61M 16/003
See application file for complete search history.

(56) References Cited

U.S. PATENT DOCUMENTS

| | | |
|---|---|---|
| 3,575,167 A | 4/1971 | Michielsen |
| 3,677,267 A | 7/1972 | Richards |
| 3,908,704 A | 9/1975 | Clement et al. |
| 4,095,592 A | 6/1978 | Delphia |
| 4,401,116 A | 8/1983 | Fry et al. |
| 4,421,113 A | 12/1983 | Gedeon et al. |
| 4,444,201 A | 4/1984 | Itoh |
| 4,702,240 A | 10/1987 | Chaoui |
| 4,721,060 A | 1/1988 | Cannon et al. |
| 4,790,832 A | 12/1988 | Lopez |

(Continued)

FOREIGN PATENT DOCUMENTS

| | | |
|---|---|---|
| EP | 521515 | 1/1993 |
| EP | 1005829 | 6/2000 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Margaret M Luarca

(57) ABSTRACT

Systems and methods for novel ventilation that allows the patient to trigger or initiate the delivery of a breath are provided. Further, systems and methods for triggering ventilation based on signal distortion of a monitored patient parameter are provided.

19 Claims, 10 Drawing Sheets

(56) References Cited

U.S. PATENT DOCUMENTS

| | | |
|---|---|---|
| 4,870,961 A | 10/1989 | Barnard |
| 5,016,626 A | 5/1991 | Jones |
| 5,074,297 A | 12/1991 | Venegas |
| 5,080,093 A | 1/1992 | Raabe et al. |
| 5,086,767 A | 2/1992 | Legal |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,148,802 A | 9/1992 | Sanders et al. |
| 5,165,398 A | 11/1992 | Bird |
| 5,174,284 A | 12/1992 | Jackson |
| 5,195,512 A | 3/1993 | Rosso |
| 5,211,170 A | 5/1993 | Press |
| 5,235,973 A | 8/1993 | Levinson |
| 5,239,995 A | 8/1993 | Estes et al. |
| 5,259,374 A | 11/1993 | Miller et al. |
| 5,273,032 A | 12/1993 | Borody |
| 5,279,549 A | 1/1994 | Ranford |
| 5,303,698 A | 4/1994 | Tobia et al. |
| 5,303,700 A | 4/1994 | Weismann et al. |
| 5,307,794 A | 5/1994 | Rauterkus et al. |
| 5,316,009 A | 5/1994 | Yamada |
| 5,318,017 A | 6/1994 | Ellison |
| 5,320,093 A | 6/1994 | Raemer |
| 5,322,057 A | 6/1994 | Raabe et al. |
| 5,323,772 A | 6/1994 | Linden et al. |
| 5,335,650 A | 8/1994 | Shaffer et al. |
| 5,373,842 A | 12/1994 | Olsson et al. |
| 5,383,448 A | 1/1995 | Tkatchouk et al. |
| 5,385,142 A | 1/1995 | Brady et al. |
| 5,395,301 A | 3/1995 | Russek |
| 5,398,676 A | 3/1995 | Press et al. |
| 5,398,682 A | 3/1995 | Lynn |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |
| 5,471,977 A | 12/1995 | Olsson et al. |
| 5,474,062 A | 12/1995 | DeVires et al. |
| 5,494,028 A | 2/1996 | DeVries et al. |
| 5,513,631 A | 5/1996 | McWilliams |
| 5,537,999 A | 7/1996 | Dearman et al. |
| 5,540,220 A | 7/1996 | Gropper et al. |
| 5,542,415 A | 8/1996 | Brody |
| 5,542,416 A | 8/1996 | Chalvignac |
| 5,551,418 A | 9/1996 | Estes et al. |
| 5,558,086 A | 9/1996 | Smith et al. |
| 5,562,918 A | 10/1996 | Stimpson |
| 5,564,416 A | 10/1996 | Jones |
| 5,582,163 A | 12/1996 | Bonassa |
| 5,590,651 A | 1/1997 | Shaffer et al. |
| 5,596,983 A | 1/1997 | Zander et al. |
| 5,603,316 A | 2/1997 | Coufal et al. |
| 5,606,968 A | 3/1997 | Mang |
| 5,632,269 A | 5/1997 | Zdrojkowski |
| 5,642,726 A | 7/1997 | Owens et al. |
| 5,647,351 A | 7/1997 | Weismann et al. |
| 5,651,361 A | 7/1997 | Dearman et al. |
| 5,655,519 A | 8/1997 | Alfery |
| 5,669,379 A | 9/1997 | Somerson et al. |
| 5,687,713 A | 11/1997 | Bahr et al. |
| 5,692,497 A | 12/1997 | Schnitzer et al. |
| 5,724,962 A | 3/1998 | Vidgren et al. |
| 5,735,267 A | 4/1998 | Tobia |
| 5,740,797 A | 4/1998 | Dickson |
| 5,765,558 A | 6/1998 | Psaros et al. |
| 5,803,065 A | 9/1998 | Zdrojkowski et al. |
| 5,806,512 A | 9/1998 | Abramov et al. |
| 5,807,245 A | 9/1998 | Aldestam et al. |
| 5,810,000 A | 9/1998 | Stevens |
| 5,813,401 A | 9/1998 | Radcliff et al. |
| 5,814,086 A | 9/1998 | Hirschberg et al. |
| 5,868,133 A | 2/1999 | DeVries et al. |
| 5,876,352 A | 3/1999 | Weismann |
| 5,878,744 A | 3/1999 | Pfeiffer |
| 5,881,725 A | 3/1999 | Hoffman et al. |
| 5,906,203 A | 5/1999 | Klockseth et al. |
| 5,911,218 A | 6/1999 | DiMarco |
| 5,915,381 A | 6/1999 | Nord |
| 5,931,160 A | 8/1999 | Gilmore et al. |
| 5,931,162 A | 8/1999 | Christian |
| 5,937,853 A | 8/1999 | Strom |
| 5,944,680 A | 8/1999 | Christopherson |
| 5,970,975 A | 10/1999 | Estes et al. |
| 5,996,580 A | 12/1999 | Swann |
| 6,015,388 A | 1/2000 | Sackner et al. |
| 6,019,100 A | 2/2000 | Alving et al. |
| 6,029,664 A | 2/2000 | Zdrojkowski et al. |
| 6,068,602 A | 5/2000 | Tham et al. |
| 6,085,747 A | 7/2000 | Axe |
| 6,095,140 A | 8/2000 | Poon et al. |
| 6,109,260 A | 8/2000 | Bathe |
| 6,112,744 A | 9/2000 | Hognelid |
| 6,131,571 A | 10/2000 | Lampotang et al. |
| 6,131,572 A | 10/2000 | Heinonen |
| 6,135,105 A | 10/2000 | Lampotang et al. |
| 6,148,814 A | 11/2000 | Clemmer et al. |
| 6,152,129 A | 11/2000 | Berthon Jones |
| 6,152,133 A | 11/2000 | Psaros et al. |
| 6,152,135 A | 11/2000 | DeVries et al. |
| 6,155,257 A | 12/2000 | Lurie et al. |
| 6,158,432 A | 12/2000 | Biondi et al. |
| 6,158,433 A | 12/2000 | Ong et al. |
| 6,192,885 B1 | 2/2001 | Jalde |
| 6,196,222 B1 | 3/2001 | Heinonen et al. |
| 6,213,119 B1 | 4/2001 | Brydon et al. |
| 6,230,708 B1 | 5/2001 | Radko |
| 6,240,920 B1 * | 6/2001 | Strom .................. A61M 16/00 128/204.23 |
| 6,257,234 B1 | 7/2001 | Sun |
| 6,260,549 B1 | 7/2001 | Sosiak |
| 6,279,569 B1 | 8/2001 | Jones |
| 6,279,574 B1 | 8/2001 | Richardson et al. |
| 6,305,372 B1 | 10/2001 | Servidio |
| 6,305,374 B1 | 10/2001 | Zdrojkowski et al. |
| 6,308,703 B1 | 10/2001 | Alving et al. |
| 6,308,706 B1 | 10/2001 | Lammers et al. |
| 6,343,603 B1 | 2/2002 | Tuck et al. |
| 6,345,619 B1 | 2/2002 | Finn |
| 6,360,740 B1 | 3/2002 | Ward et al. |
| 6,390,091 B1 | 5/2002 | Banner et al. |
| 6,390,988 B1 | 5/2002 | Robinson |
| 6,408,847 B1 | 6/2002 | Nuckols et al. |
| 6,412,482 B1 | 7/2002 | Rowe |
| 6,425,392 B1 | 7/2002 | Sosiak |
| 6,439,229 B1 | 8/2002 | Du et al. |
| 6,450,968 B1 | 9/2002 | Wallen et al. |
| 6,461,315 B1 | 10/2002 | Gattinoni |
| 6,463,930 B2 | 10/2002 | Biondi et al. |
| 6,467,477 B1 | 10/2002 | Frank |
| 6,467,479 B1 | 10/2002 | Albert et al. |
| 6,484,719 B1 | 11/2002 | Berthon Jones |
| 6,488,634 B1 | 12/2002 | Rapoport |
| 6,494,201 B1 | 12/2002 | Welik |
| 6,510,851 B2 | 1/2003 | Rydin |
| 6,516,800 B1 | 2/2003 | Bowden |
| 6,523,538 B1 | 2/2003 | Wikfeldt |
| 6,526,970 B2 | 3/2003 | DeVries et al. |
| 6,532,956 B2 | 3/2003 | Hill |
| 6,532,957 B2 | 3/2003 | Berthon Jones |
| 6,532,959 B1 | 3/2003 | Berthon Jones |
| 6,533,730 B2 | 3/2003 | Stroem |
| 6,539,938 B2 | 4/2003 | Weinstein et al. |
| 6,539,940 B2 | 4/2003 | Zdrojkowski et al. |
| 6,547,743 B2 | 4/2003 | Brydon |
| 6,553,992 B1 | 4/2003 | Berthon Jones et al. |
| 6,557,553 B1 | 5/2003 | Borrello |
| 6,564,798 B1 | 5/2003 | Jalde |
| 6,571,796 B2 | 6/2003 | Banner et al. |
| 6,575,163 B1 | 6/2003 | Berthon Jones |
| 6,575,164 B1 | 6/2003 | Jaffe et al. |
| 6,578,575 B1 | 6/2003 | Jonson |

(56) References Cited

U.S. PATENT DOCUMENTS

| | | |
|---|---|---|
| 6,581,599 B1 | 6/2003 | Stenzler |
| 6,584,973 B1 | 7/2003 | Biondi |
| 6,588,423 B1 | 7/2003 | Sinderby |
| 6,589,188 B1 | 7/2003 | Street |
| 6,595,213 B2 | 7/2003 | Bennarsten |
| 6,601,583 B2 | 8/2003 | Pessala et al. |
| 6,609,517 B1 | 8/2003 | Estes et al. |
| 6,609,518 B2 | 8/2003 | Lamb |
| 6,622,726 B1 | 9/2003 | Du |
| 6,626,175 B2 | 9/2003 | Jafari et al. |
| 6,626,176 B1 | 9/2003 | Madaus |
| 6,631,716 B1 | 10/2003 | Robinson et al. |
| 6,631,717 B1 | 10/2003 | Rich et al. |
| 6,644,310 B1 | 11/2003 | Delache et al. |
| 6,651,652 B1 | 11/2003 | Ward |
| 6,651,657 B1 | 11/2003 | Manigel |
| 6,659,101 B2 | 12/2003 | Berthon Jones |
| 6,659,961 B2 | 12/2003 | Robinson |
| 6,663,574 B2 | 12/2003 | Faram |
| 6,668,829 B2 | 12/2003 | Biondi et al. |
| 6,679,258 B1 | 1/2004 | Strom |
| 6,681,643 B2 | 1/2004 | Heinonen |
| 6,688,307 B2 | 2/2004 | Berthon Jones |
| 6,689,091 B2 | 2/2004 | Bui et al. |
| 6,694,978 B1 | 2/2004 | Bennarsten |
| 6,709,405 B2 | 3/2004 | Jonson |
| 6,722,360 B2 | 4/2004 | Doshi |
| 6,726,598 B1 | 4/2004 | Jarvis et al. |
| 6,739,336 B1 | 5/2004 | Jalde |
| 6,745,771 B2 | 6/2004 | Castor et al. |
| 6,745,773 B1 | 6/2004 | Gobel |
| 6,752,766 B2 | 6/2004 | Kowallik et al. |
| 6,752,772 B2 | 6/2004 | Kahn |
| 6,755,193 B2 | 6/2004 | Berthon Jones et al. |
| 6,758,216 B1 | 7/2004 | Berthon Jones et al. |
| 6,763,829 B2 | 7/2004 | Jaffe et al. |
| 6,786,217 B2 | 9/2004 | Stenzler |
| 6,796,305 B1 | 9/2004 | Banner et al. |
| 6,805,118 B2 | 10/2004 | Brooker et al. |
| 6,810,876 B2 | 11/2004 | Berthon Jones |
| 6,814,073 B2 | 11/2004 | Wickham |
| 6,814,075 B2 | 11/2004 | Boussignac |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,832,609 B2 | 12/2004 | Wright |
| 6,834,647 B2 | 12/2004 | Blair et al. |
| 6,837,241 B2 | 1/2005 | Samzelius |
| 6,837,242 B2 | 1/2005 | Younes |
| 6,840,240 B1 | 1/2005 | Berthon Jones et al. |
| 6,851,427 B1 | 2/2005 | Nashed |
| 6,854,462 B2 | 2/2005 | Berthon-Jones |
| 6,860,264 B2 | 3/2005 | Christopher |
| 6,860,265 B1 | 3/2005 | Emerson |
| 6,860,858 B2 | 3/2005 | Green et al. |
| 6,877,511 B2 | 4/2005 | DeVries et al. |
| 6,880,556 B2 | 4/2005 | Uchiyama |
| 6,910,480 B1 | 6/2005 | Berthon Jones |
| 6,920,875 B1 | 7/2005 | Hill et al. |
| 6,932,084 B2 | 8/2005 | Estes |
| 6,948,497 B2 | 9/2005 | Zdrojkowski et al. |
| 6,976,487 B1 | 12/2005 | Melker et al. |
| 6,990,980 B2 | 1/2006 | Richey, II |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,011,091 B2 | 3/2006 | Hill et al. |
| 7,013,892 B2 | 3/2006 | Estes et al. |
| 7,017,574 B2 | 3/2006 | Biondi et al. |
| 7,018,341 B2 | 3/2006 | Wright |
| 7,040,321 B2 | 5/2006 | Gobel et al. |
| 7,051,736 B2 | 5/2006 | Banner et al. |
| 7,055,522 B2 | 6/2006 | Berthon Jones |
| 7,066,173 B2 | 6/2006 | Banner et al. |
| 7,066,176 B2 | 6/2006 | Jaffe et al. |
| 7,080,646 B2 | 7/2006 | Wiesmann et al. |
| 7,086,098 B2 | 8/2006 | Sallvin |
| 7,089,936 B2 | 8/2006 | Madaus |
| 7,100,607 B2 | 9/2006 | Zdrojkowski et al. |
| 7,100,609 B2 | 9/2006 | Berthon Jones et al. |
| 7,121,277 B2 | 10/2006 | Ström |
| 7,128,069 B2 | 10/2006 | Farrugia et al. |
| 7,137,389 B2 | 11/2006 | Berthon Jones |
| 7,152,598 B2 | 12/2006 | Morris |
| 7,156,095 B2 | 1/2007 | Melker et al. |
| 7,159,588 B2 | 1/2007 | Wickham |
| 7,162,296 B2 | 1/2007 | Leonhardt et al. |
| 7,168,429 B2 | 1/2007 | Matthews |
| 7,191,780 B2 | 3/2007 | Faram |
| 7,210,478 B2 | 5/2007 | Banner et al. |
| 7,226,427 B2 | 6/2007 | Steen |
| 7,246,618 B2 | 7/2007 | Habashi |
| 7,255,103 B2 | 8/2007 | Bassin |
| 7,275,540 B2 | 10/2007 | Bolam et al. |
| 7,305,988 B2 | 12/2007 | Acker |
| 7,334,578 B2 | 2/2008 | Biondi et al. |
| 7,334,581 B2 | 2/2008 | Doshi |
| 7,347,205 B2 | 3/2008 | Levi |
| 7,363,925 B2 | 4/2008 | Pagan |
| 7,367,337 B2 | 5/2008 | Berthon Jones et al. |
| 7,422,015 B2 | 9/2008 | Delisle et al. |
| 7,425,201 B2 | 9/2008 | Euliano et al. |
| 7,431,035 B2 | 10/2008 | Mizuta |
| 7,445,006 B2 | 11/2008 | Dhuper et al. |
| 7,464,711 B2 | 12/2008 | Flodin |
| 7,484,508 B2 | 2/2009 | Younes |
| 7,487,774 B2 | 2/2009 | Acker |
| 7,487,775 B2 | 2/2009 | Mashak |
| 7,487,778 B2 | 2/2009 | Freitag |
| 7,509,957 B2 | 3/2009 | Duquette et al. |
| 7,523,752 B2 | 4/2009 | Montgomery et al. |
| 7,530,353 B2 | 5/2009 | Choncholas et al. |
| 7,549,421 B2 | 6/2009 | Levi et al. |
| 7,556,038 B2 | 7/2009 | Kirby et al. |
| 7,559,326 B2 | 7/2009 | Smith et al. |
| 7,572,225 B2 | 8/2009 | Stahmann et al. |
| 7,574,246 B2 | 8/2009 | Krebs et al. |
| 7,584,752 B2 | 9/2009 | Garber et al. |
| 7,588,033 B2 | 9/2009 | Wondka |
| 7,588,543 B2 | 9/2009 | Euliano et al. |
| 7,594,508 B2 | 9/2009 | Doyle |
| 7,607,432 B2 | 10/2009 | Sullivan |
| 7,610,914 B2 | 11/2009 | Bolam et al. |
| 7,617,821 B2 | 11/2009 | Hughes |
| 7,617,825 B2 | 11/2009 | Pedemonte |
| 7,624,736 B2 | 12/2009 | Borody |
| 7,634,998 B1 | 12/2009 | Fenley |
| 7,644,713 B2 | 1/2010 | Berthon Jones |
| 7,669,594 B2 | 3/2010 | Downie |
| 7,669,598 B2 | 3/2010 | Rick et al. |
| 7,678,061 B2 | 3/2010 | Lee et al. |
| 7,694,682 B2 | 4/2010 | Petersen et al. |
| 7,708,015 B2 | 5/2010 | Seeger |
| 7,717,110 B2 | 5/2010 | Kane et al. |
| 7,721,736 B2 | 5/2010 | Urias et al. |
| 7,722,546 B2 | 5/2010 | Madaus et al. |
| 7,727,160 B2 | 6/2010 | Green et al. |
| 7,731,663 B2 | 6/2010 | Averina et al. |
| 7,775,207 B2 | 8/2010 | Jaffe et al. |
| 7,798,145 B2 | 9/2010 | Weismann et al. |
| 7,802,571 B2 | 9/2010 | Tehrani |
| 7,809,442 B2 | 10/2010 | Bolea et al. |
| 7,810,496 B2 | 10/2010 | Estes |
| 7,810,497 B2 | 10/2010 | Pittman |
| 7,814,906 B2 | 10/2010 | Moretti |
| 7,819,815 B2 | 10/2010 | Younes |
| 7,841,341 B2 | 11/2010 | Dhuper et al. |
| 7,841,343 B2 | 11/2010 | Deane |
| 7,865,244 B2 | 1/2011 | Giftakis et al. |
| 7,866,318 B2 | 1/2011 | Bassin |
| 7,891,353 B2 | 2/2011 | Chalvignac |
| 7,905,231 B2 | 3/2011 | Chalvignac |
| 7,914,459 B2 | 3/2011 | Green |

(56) References Cited

U.S. PATENT DOCUMENTS

| | | |
|---|---|---|
| 7,918,226 B2 | 4/2011 | Acker |
| 7,934,499 B2 | 5/2011 | Berthon-Jones |
| 7,934,500 B2 | 5/2011 | Madaus |
| 7,938,114 B2 | 5/2011 | Matthews |
| 7,942,823 B2 | 5/2011 | Wright |
| 7,984,712 B2 | 7/2011 | Soliman |
| 8,015,974 B2 | 9/2011 | Christopher |
| 8,020,555 B2 | 9/2011 | Rapoport |
| 8,020,558 B2 | 9/2011 | Christopher |
| 8,021,309 B2 | 9/2011 | Zilberg |
| 8,025,052 B2 | 9/2011 | Matthews |
| 8,051,852 B2 | 11/2011 | Bassin |
| 8,061,354 B2 | 11/2011 | Schneider |
| 8,066,003 B2 | 11/2011 | Cong |
| 8,122,883 B2 | 2/2012 | Banner |
| 8,136,521 B2 | 3/2012 | Matthews |
| 8,157,743 B2 | 4/2012 | Schaetzl |
| 8,160,817 B2 | 4/2012 | Ranieri |
| 8,186,344 B2 | 5/2012 | Bonassa |
| 8,220,456 B2 | 7/2012 | Kane |
| 8,225,789 B2 | 7/2012 | Berthon-Jones |
| 8,261,742 B2 | 9/2012 | Strothmann |
| 8,312,879 B2 | 11/2012 | Choncholas |
| 8,316,847 B2 | 11/2012 | Hallett |
| 8,353,844 B2 | 1/2013 | Jin |
| 8,381,724 B2 | 2/2013 | Bowen |
| 8,381,729 B2 | 2/2013 | Freitag |
| 8,388,548 B2 | 3/2013 | Green |
| 8,397,720 B2 | 3/2013 | Eger |
| 8,408,205 B2 | 4/2013 | Madaus |
| 8,424,524 B2 | 4/2013 | Heinonen |
| 8,443,801 B2 | 5/2013 | Soliman |
| 8,485,982 B2 | 7/2013 | Gavish |
| 8,522,781 B2 | 9/2013 | Schneider |
| 8,528,553 B2 | 9/2013 | Wysocki |
| 8,550,077 B2 | 10/2013 | Chatburn |
| 8,555,880 B2 | 10/2013 | Boring |
| 8,573,205 B2 | 11/2013 | Habashi |
| 8,573,207 B2 | 11/2013 | Gutierrez |
| 8,603,006 B2 * | 12/2013 | Mulqueeny .......... A61B 5/0871 600/533 |
| 8,617,083 B2 | 12/2013 | Euliano |
| 8,646,447 B2 | 2/2014 | Martin |
| 8,652,065 B2 | 2/2014 | Titchener |
| 8,672,858 B2 | 3/2014 | Euliano |
| 8,689,791 B2 | 4/2014 | Hayek |
| 8,695,597 B2 | 4/2014 | Glaw |
| 8,701,665 B2 | 4/2014 | Tehrani |
| 8,707,953 B2 | 4/2014 | Wickham |
| 8,783,247 B2 | 7/2014 | Newman, Jr. |
| 8,826,906 B2 | 9/2014 | Bassin |
| 8,869,795 B2 | 10/2014 | Bassin |
| 8,893,717 B2 | 11/2014 | Montgomery |
| 8,899,231 B2 | 12/2014 | Bassin |
| 8,899,232 B2 | 12/2014 | Farrugia |
| 8,910,632 B2 | 12/2014 | Tiedje |
| 8,920,333 B2 | 12/2014 | Younes |
| 8,925,545 B2 | 1/2015 | Wondka |
| 8,944,057 B2 | 2/2015 | Hill |
| 8,985,107 B2 | 3/2015 | Viertiö-Oja |
| 8,985,109 B2 | 3/2015 | Bateman |
| 9,016,277 B2 | 4/2015 | Kniewasser |
| 9,078,984 B2 | 7/2015 | Poon |
| 9,114,222 B2 | 8/2015 | Bliss |
| 9,192,323 B2 | 11/2015 | Heyer |
| 9,205,210 B2 | 12/2015 | Bassin |
| 9,216,262 B2 | 12/2015 | Desforges |
| 9,220,856 B2 | 12/2015 | Martin |
| 9,238,114 B2 | 1/2016 | Eger |
| 9,259,544 B2 | 2/2016 | Kane |
| 9,272,106 B2 | 3/2016 | Sibenaller |
| 9,295,796 B2 | 3/2016 | Eklund |
| 9,295,797 B2 | 3/2016 | Shissler |
| 9,320,863 B2 | 4/2016 | Balko |
| 9,333,312 B2 | 5/2016 | Cardelius |
| 9,392,963 B2 | 7/2016 | Krans |
| 9,392,964 B2 | 7/2016 | Mulqueeny |
| 9,504,795 B2 | 11/2016 | Bassin |
| 9,555,204 B2 | 1/2017 | Rahlf |
| 9,592,356 B2 | 3/2017 | Truschel |
| 9,597,467 B2 | 3/2017 | Zheng |
| 9,636,474 B2 | 5/2017 | Mulqueeny |
| 9,655,544 B2 | 5/2017 | Stenqvist |
| 9,682,208 B2 | 6/2017 | Ramanan |
| 9,713,690 B2 | 7/2017 | Somaiya |
| 9,757,270 B2 | 9/2017 | Carrubba |
| 9,827,387 B2 | 11/2017 | Schneider |
| 9,839,760 B2 | 12/2017 | Bonassa |
| 9,848,831 B2 | 12/2017 | Nonaka |
| 9,925,346 B2 | 3/2018 | Dong |
| 9,968,750 B2 | 5/2018 | Sinderby |
| 9,980,943 B2 | 5/2018 | Burkin |
| 9,987,444 B2 | 6/2018 | Colbaugh |
| 9,987,445 B2 | 6/2018 | Ahmad |
| 10,004,862 B2 | 6/2018 | Armitstead |
| 10,022,084 B2 | 7/2018 | Nonaka |
| 10,022,512 B2 | 7/2018 | Tiedje |
| 10,065,007 B2 | 9/2018 | Troili |
| 10,137,266 B2 | 11/2018 | Shelly |
| 10,165,966 B2 | 1/2019 | Banner |
| 10,179,218 B2 | 1/2019 | Ahmad |
| 10,207,068 B2 | 2/2019 | Jafari |
| 10,293,126 B2 | 5/2019 | Berry Ann |
| 10,314,515 B2 | 6/2019 | Colman |
| 10,335,566 B2 | 7/2019 | Kulstad |
| 10,342,457 B2 | 7/2019 | Spencer |
| 10,357,624 B2 | 7/2019 | Van Der Staay |
| 2001/0004893 A1 | 6/2001 | Biondi et al. |
| 2001/0007255 A1 | 7/2001 | Stumpf |
| 2002/0023640 A1 | 2/2002 | Nightengale |
| 2002/0026941 A1 | 3/2002 | Biondi et al. |
| 2002/0046753 A1 | 4/2002 | Lamb |
| 2002/0073993 A1 | 6/2002 | Weinstein et al. |
| 2002/0174866 A1 | 11/2002 | Orr et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0125662 A1 | 7/2003 | Bui |
| 2003/0131848 A1 | 7/2003 | Stenzler |
| 2003/0136402 A1 | 7/2003 | Jiang et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0178024 A1 | 9/2003 | Allan et al. |
| 2003/0192544 A1 | 10/2003 | Berthon Jones et al. |
| 2004/0016431 A1 | 1/2004 | Preveyraud |
| 2004/0050387 A1 | 3/2004 | Younes |
| 2004/0103896 A1 | 6/2004 | Jafari et al. |
| 2004/0159323 A1 | 8/2004 | Schmidt et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0231670 A1 | 11/2004 | Bassin |
| 2005/0022809 A1 | 2/2005 | Wondka |
| 2005/0027252 A1 | 2/2005 | Boukas |
| 2005/0061318 A1 | 3/2005 | Faram |
| 2005/0076907 A1 | 4/2005 | Stenzler |
| 2005/0098179 A1 | 5/2005 | Burton et al. |
| 2005/0103331 A1 | 5/2005 | Wedemeyer |
| 2005/0109339 A1 | 5/2005 | Stahmann et al. |
| 2005/0109340 A1 | 5/2005 | Tehrani |
| 2005/0126565 A1 | 6/2005 | Huang |
| 2005/0133028 A1 | 6/2005 | Pagan |
| 2005/0199237 A1 | 9/2005 | Lurie |
| 2005/0217671 A1 | 10/2005 | Fisher et al. |
| 2005/0241639 A1 | 11/2005 | Zilberg |
| 2005/0263152 A1 | 12/2005 | Fong |
| 2005/0279358 A1 | 12/2005 | Richey, II |

(56) References Cited

U.S. PATENT DOCUMENTS

| | | |
|---|---|---|
| 2005/0284469 A1 | 12/2005 | Tobia et al. |
| 2006/0011195 A1 | 1/2006 | Zarychta |
| 2006/0032497 A1 | 2/2006 | Doshi |
| 2006/0094972 A1 | 5/2006 | Drew |
| 2006/0102180 A1 | 5/2006 | Berthon Jones |
| 2006/0162727 A1 | 7/2006 | Biondi et al. |
| 2006/0178245 A1 | 8/2006 | Schiller et al. |
| 2006/0201507 A1 | 9/2006 | Breen |
| 2006/0249148 A1 | 11/2006 | Younes |
| 2006/0249155 A1 | 11/2006 | Gambone |
| 2006/0272642 A1 | 12/2006 | Chalvignac |
| 2006/0276718 A1 | 12/2006 | Madaus et al. |
| 2006/0278221 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2007/0000494 A1 | 1/2007 | Banner et al. |
| 2007/0017518 A1 | 1/2007 | Farrugia et al. |
| 2007/0028921 A1 | 2/2007 | Banner et al. |
| 2007/0044796 A1 | 3/2007 | Zdrojkowski et al. |
| 2007/0062529 A1 | 3/2007 | Choncholas et al. |
| 2007/0113843 A1 | 5/2007 | Hughes |
| 2007/0144523 A1 | 6/2007 | Bolam et al. |
| 2007/0151563 A1 | 7/2007 | Ozaki et al. |
| 2007/0163590 A1 | 7/2007 | Bassin |
| 2007/0181122 A1 | 8/2007 | Mulier |
| 2007/0186928 A1 | 8/2007 | Be'Eri |
| 2007/0191787 A1 | 8/2007 | Lim et al. |
| 2007/0208267 A1 | 9/2007 | Schmid et al. |
| 2007/0221222 A1 | 9/2007 | Lurie |
| 2007/0225623 A1 | 9/2007 | Freeman |
| 2007/0227538 A1 | 10/2007 | Scholler et al. |
| 2007/0227539 A1 | 10/2007 | Schwaibold et al. |
| 2007/0267015 A1 | 11/2007 | Thoemmes et al. |
| 2007/0272243 A1 | 11/2007 | Sherman et al. |
| 2007/0277825 A1 | 12/2007 | Bordewick et al. |
| 2008/0000471 A1 | 1/2008 | Bolam et al. |
| 2008/0000475 A1 | 1/2008 | Hill |
| 2008/0000478 A1 | 1/2008 | Matthiessen et al. |
| 2008/0011294 A1 | 1/2008 | Heesch et al. |
| 2008/0017198 A1 | 1/2008 | Ivri |
| 2008/0029096 A1 | 2/2008 | Kollmeyer et al. |
| 2008/0033304 A1 | 2/2008 | Dalal et al. |
| 2008/0035146 A1 | 2/2008 | Crabb |
| 2008/0041382 A1 | 2/2008 | Matthews et al. |
| 2008/0092894 A1 | 4/2008 | Nicolazzi et al. |
| 2008/0097234 A1 | 4/2008 | Nicolazzi et al. |
| 2008/0115786 A1 | 5/2008 | Sinderby et al. |
| 2008/0125828 A1 | 5/2008 | Ignagni et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0163872 A1 | 7/2008 | Negele et al. |
| 2008/0178880 A1 | 7/2008 | Christopher et al. |
| 2008/0178882 A1 | 7/2008 | Christopher et al. |
| 2008/0216833 A1 | 9/2008 | Pujol et al. |
| 2008/0251078 A1 | 10/2008 | Buckley et al. |
| 2008/0257337 A1 | 10/2008 | Denyer et al. |
| 2008/0275513 A1 | 11/2008 | Lattner et al. |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0294060 A1 | 11/2008 | Haro et al. |
| 2008/0295839 A1 | 12/2008 | Habashi |
| 2008/0295840 A1 | 12/2008 | Glaw |
| 2009/0013999 A1 | 1/2009 | Bassin |
| 2009/0056709 A1 | 3/2009 | Worsoff |
| 2009/0120439 A1 | 5/2009 | Goebel |
| 2010/0116270 A1 | 5/2010 | Edwards et al. |
| 2010/0125227 A1 | 5/2010 | Bird |
| 2010/0186744 A1 | 7/2010 | Andrieux |
| 2010/0229863 A1 | 9/2010 | Enk |
| 2010/0236551 A1 | 9/2010 | Enk |
| 2010/0263669 A1 | 10/2010 | Bowsher |
| 2011/0011403 A1 | 1/2011 | Hannah et al. |
| 2016/0114115 A1* | 4/2016 | Glenn ................ G16H 40/63 128/204.23 |
| 2016/0228282 A1 | 8/2016 | Carrubba |
| 2016/0243324 A1 | 8/2016 | Doyle |
| 2016/0250427 A1 | 9/2016 | Jafari |
| 2016/0256643 A1 | 9/2016 | Graboi |
| 2016/0256656 A1 | 9/2016 | Glenn |
| 2016/0287822 A1* | 10/2016 | Masic ................ A61M 16/021 |
| 2016/0354566 A1 | 12/2016 | Thiessen |
| 2017/0095627 A1 | 4/2017 | Jafari |
| 2017/0164872 A1 | 6/2017 | Sanborn |
| 2017/0182269 A1 | 6/2017 | Masic |
| 2017/0296765 A1 | 10/2017 | Dong |
| 2018/0036500 A1 | 2/2018 | Esmaeil-zadeh-azar |
| 2018/0193578 A1 | 7/2018 | Glenn |
| 2018/0207378 A1 | 7/2018 | Masic |
| 2018/0207379 A1 | 7/2018 | Masic |
| 2018/0304034 A1 | 10/2018 | Vicario et al. |
| 2018/0325459 A1 | 11/2018 | Nakai |
| 2019/0143058 A1 | 5/2019 | Gardner |
| 2019/0274585 A1 | 9/2019 | Milne |

FOREIGN PATENT DOCUMENTS

| | | |
|---|---|---|
| EP | 1005830 | 6/2000 |
| EP | 996358 | 1/2002 |
| EP | 1277435 | 1/2003 |
| WO | WO 2008/008659 | 1/2008 |
| WO | WO 2008/021222 | 2/2008 |
| WO | WO 2008/113752 | 9/2008 |
| WO | WO 2009/060330 | 5/2009 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Boitano, Louis J., "An Evaluation of Home vol. Ventilators That Support OpenCircuit Mouthpiece Ventilation", Respiratory Care, Nov. 2005, vol. 50, No. 11, pp. 1457-1461.

Puritan Bennett 980 Series Ventilator Operator's Manual, Covidien, Jan. 29, 2014, Part. No. 10077893 A Jan. 2014, 506 pages.

PCT International Search Report and Written Opinion in International Application PCT/US2019/032280, dated Jul. 30, 2019, 15 pgs.

* cited by examiner

SYSTEMS AND METHODS FOR RESPIRATORY EFFORT DETECTION UTILIZING SIGNAL DISTORTION

RELATED APPLICATIONS

This application claims the benefit of U.S. Provisional Application Ser. No. 62/671,063, filed May 14, 2018, and further claims the benefit of U.S. Provisional Application Ser. No. 62/740,740, filed Oct. 3, 2018, the complete disclosures of which are hereby incorporated herein by reference in their entirety.

BACKGROUND

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different breath modes or settings have been created to provide better ventilation for patients in different scenarios, such as mandatory ventilation modes and spontaneous ventilation modes.

It is with respect to this general technical environment that aspects of the present technology disclosed herein have been contemplated. Although a general environment has been discussed, it should be understood that the examples described herein should not be limited to the general environment identified herein.

SUMMARY

Aspects of the disclosure relate to providing novel systems and methods for beginning (triggering) or ending (cycling) inspiration or changing settings during mechanical ventilation of a patient. More specifically, this disclosure describes systems and methods for controlling ventilation based on a change in characteristics of a patient parameter signal, such as a signal distortion, changed signal properties, a degradation, or a shift.

It is to be understood that both the foregoing general description and the following detailed description are exemplary and explanatory and are intended to provide further explanation of the invention as claimed.

In an aspect, a method for triggering inhalation during spontaneous or assisted ventilation of a patient on a mechanical ventilator is provided. The method includes monitoring, during an exhalation phase, a physiologic parameter signal of a patient receiving ventilation on a mechanical ventilator, and tracking a distortion indicator in the physiological parameter signal. The method further includes applying a sensitivity check to the distortion indicator and detecting a patient inhalation effort in response to the sensitivity check. Additionally, the method includes triggering an inhalation by the mechanical ventilator in response to the detected patient inhalation effort.

In another aspect, a method for triggering inhalation during spontaneous or assisted ventilation of a patient on a mechanical ventilator is provided. The method includes monitoring, during an exhalation phase, a flow or pressure signal of a patient receiving ventilation on a mechanical ventilator and tracking a distortion indicator in the flow or pressure signal. The method further includes dynamically updating the distortion indicator during the exhalation phase and detecting a patient inhalation effort from the distortion indicator before the flow or pressure signal has crossed a trigger baseline. Additionally, the method includes triggering an inhalation by the mechanical ventilator as a result of the detected patient inhalation effort.

In yet another aspect, a method for triggering inspiration during spontaneous or assisted ventilation of a patient on a ventilator is provided. The method includes monitoring, from one or more non-invasive sensors during exhalation, a physiological parameter signal of a patient receiving ventilation from a ventilator and determining, by a microprocessor, an energy metric of the physiological parameter signal. The method further includes determining, by the microprocessor, that the energy metric exhibits a deviation and determining, by the microprocessor, that the deviation satisfies a trigger condition. Additionally, the method includes detecting, in response to the satisfied trigger condition, a patient effort to inhale and triggering inspiration in response to the detection of the patient effort.

BRIEF DESCRIPTION OF THE DRAWINGS

The following drawing figures, which form a part of this application, are illustrative of aspects of systems and methods described below and are not meant to limit the scope of the invention in any manner, which scope shall be based on the claims.

DETAILED DESCRIPTION

Figure 1:
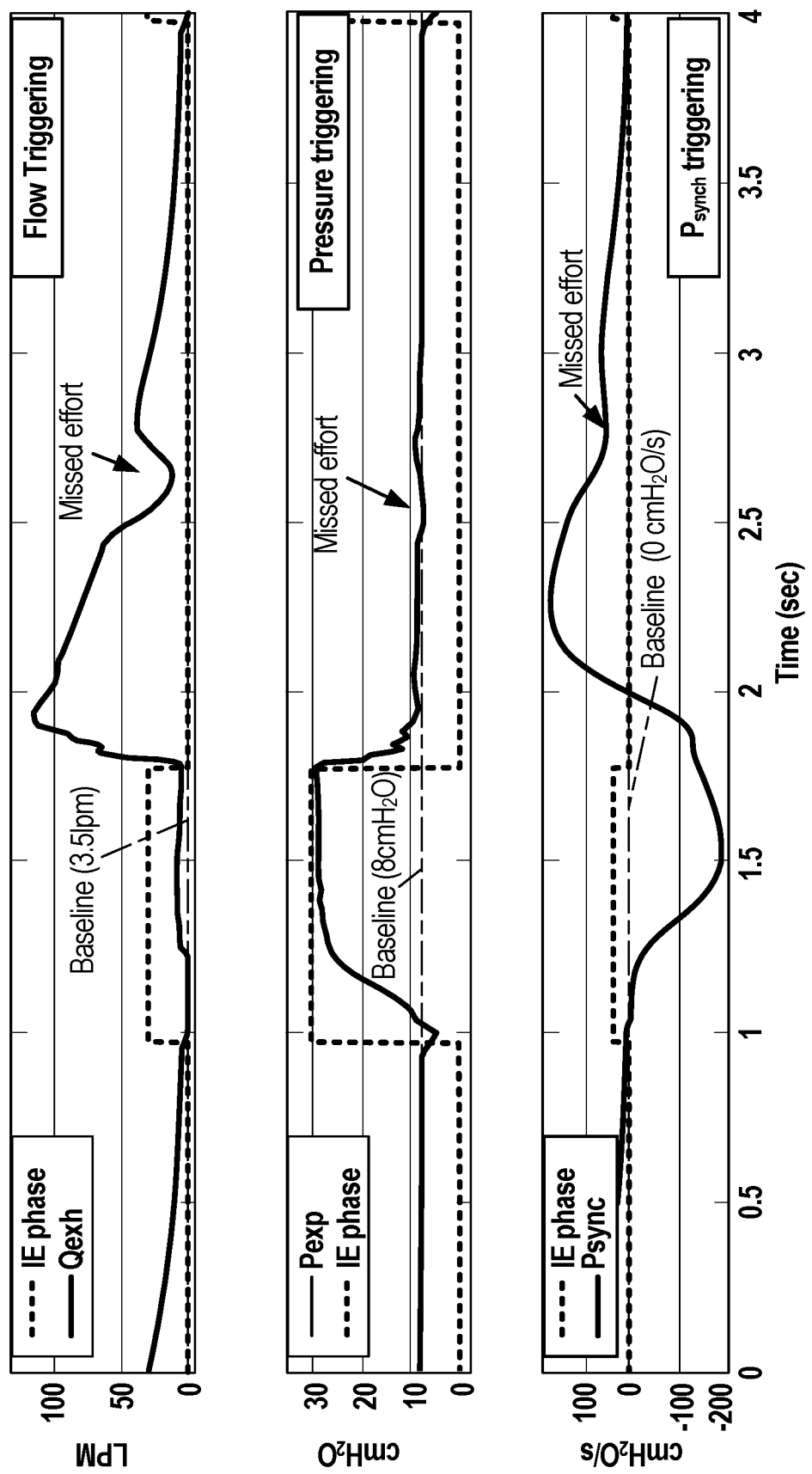
FIG. 1 is a set of charts illustrating signal distortion from a patient effort to inhale during ventilation by flow, pressure, and Psync triggers, in accordance with aspects of the disclosure.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with many systems such as ventilators for non-human patients, invasive or non-invasive ventilation, and other gas transport systems, and various types of event detection.

Medical ventilators are used to provide a breathing gas to a patient who may otherwise be unable to breathe sufficiently. In modern medical facilities, pressurized air and oxygen sources are often available from wall outlets or pressurized tanks. Accordingly, ventilators may provide control valves (limiting or regulating pressure or flow) connected to sources of pressurized air and pressurized oxygen. The flow valves function to regulate flow so that respiratory gas having a desired concentration of oxygen is supplied to the patient at desired pressures and flow rates. Ventilators capable of operating independently of external sources of pressurized air are also available (such as ventilators with pumps, blowers, and/or fans).

As each patient may require a different ventilation strategy, modern ventilators can be customized for the particular needs of an individual patient. For example, several different ventilator modes, breath types, and/or settings have been created to provide clinically appropriate ventilation for patients in various different scenarios, such as mandatory ventilation modes and assist control ventilation modes. Assist control modes (also referred to herein as "spontaneous modes") allow a spontaneously breathing patient to trigger inspiration during ventilation. In a spontaneous or assisted mode of ventilation, the ventilator begins (triggers) inspiration upon the detection of patient demand or patient effort to inhale. The ventilator ends inspiration and begins expiration (cycles to expiration) when a threshold is met or when a patient demand or effort for exhalation is detected.

The performance of a medical ventilator in responding to a patient effort to begin a new inspiration (trigger inhalation) or a patient effort to end an inspiration (cycle to exhalation) represents an important characteristic of a medical ventilator. A ventilator's inspiration trigger and exhalation cycle response impact the patient's work of breathing and the overall patient-ventilator synchrony. The trigger and cycle responses of a ventilator are a function of a patient's inspiratory and expiratory behavior (breathing effort magnitude and timing characteristics), as well as the ventilator's gas delivery dynamics and flow control parameters (actuator response, delay, etc.).

Triggering delay time, cycling delay time, asynchrony index, metabolic work, pressure-time product, and other parameters are used to measure the patient-ventilator synchrony. The asynchrony index is the ratio between the number of asynchronous events and the total respiratory rate. Miss-triggering ("missing" a trigger by failing to provide inspiration in response to a patient demand to inhale) or delayed cycling ("missing" a cycle to exhalation by failing to provide exhalation in response to a patient demand to exhale) can increase the patient-ventilator asynchrony index. Similarly, auto-triggering (providing inhalation too early) and premature cycling (providing exhalation too early) can also increase the asynchrony index. Several different factors cause asynchrony events, such as variation in patient's breathing pattern, muscle strength, respiratory mechanics, ventilator performance, and ventilator characteristics.

In some conventional triggering modes, a patient's inspiratory trigger is detected based on the magnitude of deviations (deviations generated by a patient's inspiratory effort) of a measured parameter from a determined baseline. For example, in flow triggering, the patient's inspiration effort is detected when the measured patient exhalation flow value drops below a flow baseline (i.e. the base flow) by a set amount (based on the triggering sensitivity). In pressure triggering, the patient's inspiration effort is detected when the measured expiratory pressure value drops below a pressure baseline (for example, the set PEEP value) by a set amount (based on triggering sensitivity). Another parameter that can be used for triggering is a derived signal such as the Psync signal, which is an estimation of the rate of change of the patient's interpleural pressure or muscle pressure (Pmus), or an estimation of the rate of change of pressure at the diaphragm, indicative of a patient's effort to breathe. In Psync triggering, the patient's inspiration effort is detected when the Psync signal value drops below baseline by a set amount (based on the triggering sensitivity). In each case (pressure, flow, Psync, or other parameter signal), the triggering sensitivity can be adjusted to increase or decrease the amount by which the signal must pass the baseline before the ventilator recognizes a patient effort and triggers inspiration. Decreasing the amount increases sensitivity (as the ventilator detects a patient effort at lower magnitudes of deviation) and increasing the amount decreases sensitivity (as the ventilator does not detect a patient effort until a larger magnitude of deviation is present).

These triggering approaches compare the value of a selected parameter signal to a baseline or threshold value. This baseline is set at a level that is intended to indicate the presence of the patient's respiratory effort. However, a major limitation of these triggering types is that they may fail to detect a patient's effort if the effort occurs before the current exhalation has completed or before the baseline is reached by the signal. In this case, additional exhalation time is needed for the signal value to drop below its baseline by the sensitivity amount, in order to trigger a new inspiration. This additional exhalation may require more time and/or more patient work of breathing (such as the patient actively pushing to exhale faster). Such additional time may cause long trigger delay or even a missed trigger. Further, the requirement of more work of breathing may cause patient discomfort.

Missed inspiration triggering is particularly prevalent during the ventilation of chronic obstructive pulmonary disease (COPD) patients or in patients with rapid breathing (or high breath rate). COPD patients or patients with high breath rates may demand another breath before they have fully exhaled. As a result, traditional triggering systems and methods may not detect inspiratory efforts from these patients because the effort occurs before the measured parameter signal has returned to its set baseline.

Three examples of a missed trigger are shown in FIG. 1. The upper graph of FIG. 1 shows exhalation flow (Qexh) (dark line) plotted as lpm (liters per minute) over time. The graph also shows the phase of ventilation (dotted line raised during inhalation and lowered during exhalation). During exhalation, the flow waveform drops as the rate of exhalation flow decreases. In a flow triggering mode, the ventilator is programmed to end exhalation and trigger a new inspiration when this flow waveform passes a baseline. However, as shown in FIG. 1, the patient makes an inhalation effort before the end of the exhalation phase. This effort is visible where the flow waveform dips downward, as the patient attempts to draw air inward (and thus exhalation flow decreases). Because the flow waveform does not pass below the baseline threshold, the ventilator does not trigger a new breath, and the result is a missed trigger. The patient demanded a new breath, but the ventilator did not trigger inspiration. In particular, in the top graph of FIG. 1, the baseline was set at 3.5 lpm, with a sensitivity of 2 lpm (the amount by which the flow must drop below the baseline in order for the ventilator to detect a trigger). The patient effort was missed because the flow waveform did not drop below 1.5 lpm (which is 2 lpm below the set baseline of 3.5 lpm).

A similar missed trigger is shown in the middle graph of FIG. 1, which shows a pressure triggering type with a pressure sensitivity of 2 $cmH_2O$ and a baseline of 8 $cmH_2O$. The patient's inspiratory effort was missed because the expiratory pressure (Pexp) did not drop below 6 $cmH_2O$ (which is 2 $cmH_2O$ below the set baseline of 8 $cmH_2O$).

The lower most graph in FIG. 1 shows a Psync trigger type with a triggering sensitivity of 2 $cmH_2O/s$ and a baseline of 0 $cmH_2O/s$. The patient's inspiratory effort was missed because the Psync signal did not drop below −2 $cmH_2O/s$ (which is 2 $cmH_2O/s$ below the set baseline of 0 $cmH_2O/s$).

Figure 2:
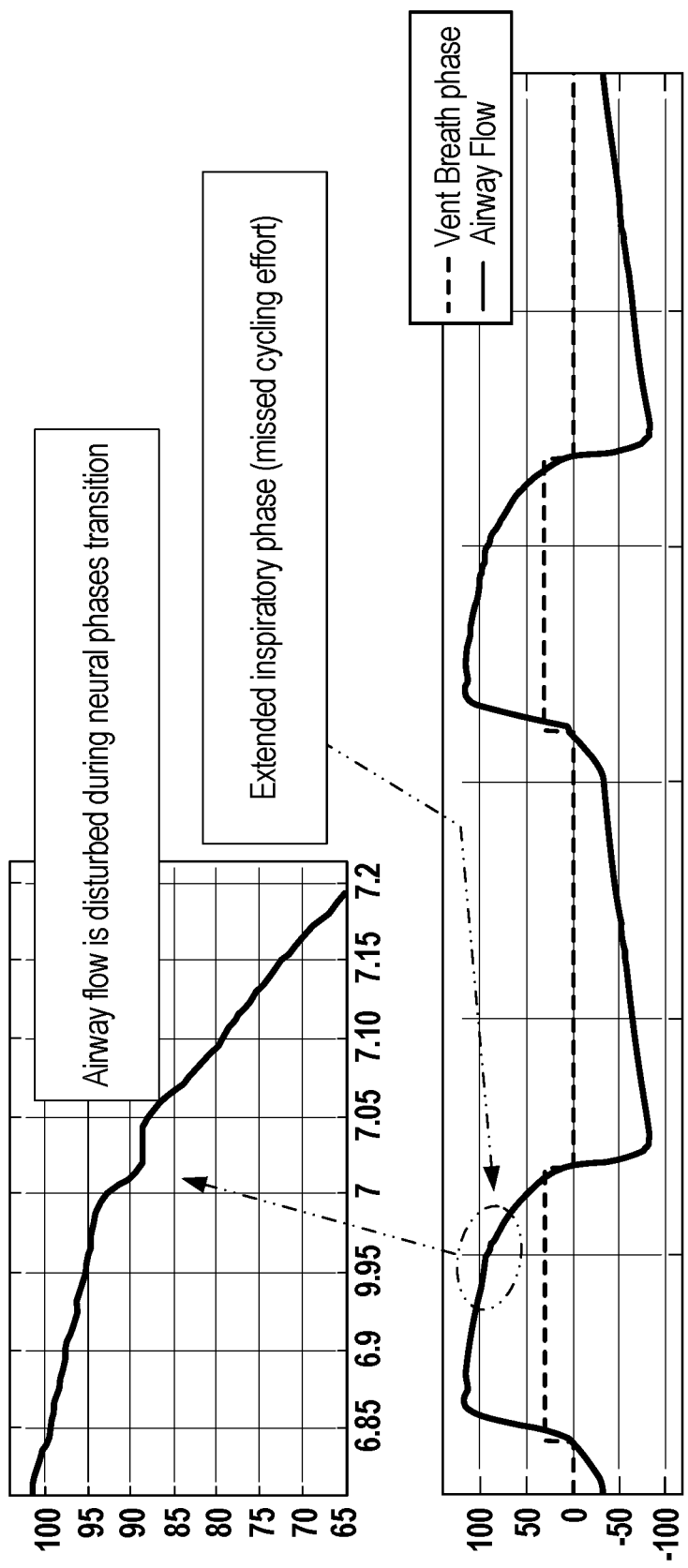
FIG. 2 is a set of charts illustrating signal distortion from a patient effort to exhale during ventilation by flow trigger, in accordance with aspects of the disclosure.

An example of delayed cycling is shown in FIG. 2. The graphs in FIG. 2 illustrate a flow waveform during inhalation (phase waveform elevated) and exhalation (phase waveform at zero). During the inhalation phase, the flow waveform is disturbed (see enlarged box) when the patient attempts to exhale. However, because the rate of flow did not drop below a defined baseline, the ventilator did not detect the patient's effort to exhale. Accordingly, the portion of the inhalation phase after that flow disturbance is an extended inhalation beyond the patient desire to exhale. This extended inhalation phase is a form of asynchrony between the patient and ventilator.

The systems and methods described herein provide improved ventilation systems and methods, including systems and methods for inspiration triggering and exhalation cycling and control of ventilation settings. According to an embodiment, a ventilation control system detects a change in characteristic—such as a shift, disturbance, or distortion—of a monitored patient parameter, instead of comparing a monitored patient parameter to a baseline. This approach may be referred to as signal distortion tracking, signal distortion triggering, or signal distortion cycling.

According to an embodiment, when a patient attempts to inhale or exhale, the effort from the patient causes a disturbance which results in a distortion in a measured or calculated signal. For example, the patient effort causes the flow, pressure, Psync, or other monitored, derived, or calculated signal to distort from its prior shape or status. "Distortion" means a detectable change in shape of the signal that alters its basic components or structure. This detectable change can include various shifts and changes, and is not limited to instances of noise or degradation. When the signal distorts, various metrics such as signal energy, signal to noise ratio, frequency content, morphology, and others (examples described more fully below) change as compared to the signal prior to the distortion. This distortion can be detected before the signal has returned to a baseline level. As such, the distortion tracking system tracks one or more distortion metrics or distortion indicators of a monitored patient parameter and detects distortion when a patient attempts to inhale or exhale.

In an embodiment, distortion is detected in a physiological parameter signal that is measured from a sensor, or calculated, or derived. The signal can be any suitable signal that exhibits distortion based on patient effort to breathe (inhale or exhale). Exemplary signals include inspiratory flow rate, expiratory flow rate, net flow, lung flow, inspiratory pressure, expiratory pressure, Psync, esophageal pressure, muscle pressure, estimates of esophageal pressure, diaphragm effort (such as from an EEG signal), delivered volume, estimations of patient effort other patient parameters, derived parameters, or combinations of two or more of these signals. In an embodiment, the signal is expiratory flow measured by a flow sensor internal or external to the ventilator. In an embodiment, the signal is expiratory pressure measured by a pressure sensor internal or external to the ventilator. This list is exemplary only and is not meant to be limiting.

By detecting distortion, the system can detect a patient effort before the monitored signal returns to a baseline level. Thus, the distortion tracking system can detect patient efforts to inhale before the end of exhalation phase and can detect patient efforts to exhale before the end of inhalation phase. The distortion tracking system can reduce the occurrence of missed efforts (missed triggers to inhale or missed cycles to exhale) that take place before the end of the phase, and can improve trigger or cycle response time and reduce patient effort, as compared to conventional trigger/cycle systems that compare a signal to a baseline. The distortion tracking system can improve patient-ventilator synchrony by improving inspiration trigger and/or exhalation cycling detection. Also, the distortion tracking system monitors for distortion dynamically within each breath, rather than by reference to a fixed baseline, and thus can automatically adapt to a patient through changing clinical conditions (surgery, recovery, etc).

While the distortion tracking system is referred to herein as a triggering or cycling type, it may also be referred to as a triggering or cycling mode, breath type or mode, supplemental breath type or mode, or ventilation mode. It is utilized in conjunction with or in addition to any spontaneous mode of ventilation running any suitable breath type for a spontaneous mode of ventilation (including assist modes).

Figure 3:
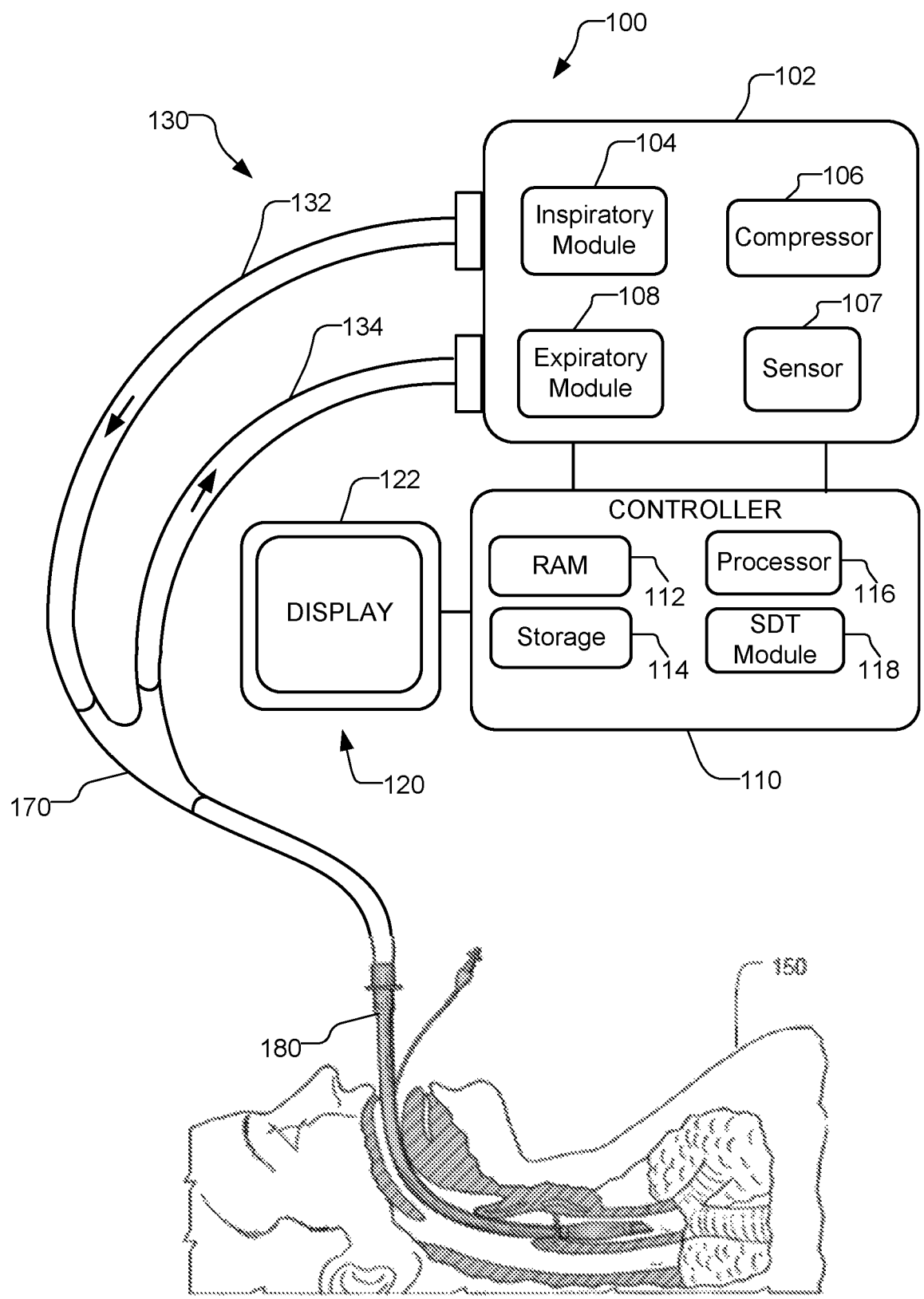
FIG. 3 is a schematic diagram illustrating a ventilator with a signal distortion tracking system, in accordance with aspects of the disclosure.

In an embodiment, a distortion tracking system is provided in a medical ventilator, as shown in FIG. 3. FIG. 3 illustrates a schematic diagram of an aspect of an exemplary ventilator 100 connected to a human patient 150. Ventilator 100 includes a signal distortion tracking (SDT) module 118. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown, or other airway tubes such as tracheostomy tubes) or a non-invasive (e.g., nasal mask or prongs) patient interface 180. Pneumatic system 102 includes an expiratory module 108 and an inspiratory module 104. The ventilator 100 also includes one or more sensors 107 such as pressure, flow, temperature, and other sensors communicatively coupled to the ventilator.

In an embodiment, the sensors 107 are non-invasive to the patient. In an embodiment, the non-invasive sensors 107 are non-contact, meaning they do not physically touch the patient. In an embodiment, the sensors 107 are located within the mechanical ventilator 100. Sensors are referred to as non-invasive when the sensors are located externally to patient. For example, sensors located in the patient wye 170, in the expiratory module 108, in the inspiratory module 104, or on the patient's finger are all external to the patient and are non-invasive. Sensors are referred to herein as invasive when the sensors are located within the patient or placed inside the patient's body, such as sensors located in an endotracheal tube, near a patient diaphragm, or on an esophageal balloon. While invasive sensors can provide great patient data or measurements, these sensors can often be hard to maintain or keep properly positioned. In an embodiment, the signal distortion methods for triggering, cycling, and other actions on the ventilator are accomplished with non-invasive and/or non-contact sensors, and without adding any additional sensors to the ventilator 100.

In an embodiment, the SDT module 118 monitors the parameter signal at each sample period. The sample period as used herein refers to a discrete period of time used to monitor a physiological parameter. In some aspects, the sample period is a computation cycle for the ventilator 100. In some aspects, the sample period is every 1 milliseconds (ms), 2 ms, 3 ms, 4 ms, 5 ms, 10 ms, 15 ms, 20 ms, 25 ms, 30 ms, 50 ms, 100 ms, or other similar period. This list is exemplary only and is not meant to be limiting. Any suitable sample period for monitoring a physiological parameter of the patient may be utilized by the ventilator 100 as would be understood by a person of skill in the art. In an embodiment, the SDT module 118 receives a sensor output (such as a raw or filtered measurement from a sensor 107), determines the physiological parameter from the sensor output (such as calculating a flow waveform from a flow sensor measurement), and provides the physiological parameter to other components of the ventilator 100 (such as pneumatic system 102, expiratory module 108, inspiratory module 104, processor 116, or controller 110). Alternatively, the SDT module 118 receives the calculated physiological parameter (such as a flow waveform) calculated elsewhere in the system (such as pneumatic system 102, expiratory module 108, inspiratory module 104, processor 116, or controller 110).

Examples below are given for using signal distortion detection to trigger (begin inhalation phase) and cycle (begin exhalation phase), and to perform other actions.

According to an embodiment, a ventilator includes a signal distortion tracking system that monitors signal distortion of a monitored patient parameter to detect patient triggering efforts (efforts to end exhalation and start inhalation) and/or to determine if the set triggering threshold is appropriate for the patient. According to an embodiment, the SDT module 118 monitors a physiological parameter of the patient to identify when a distortion due to patient effort is present in the signal. The physiological parameter may be any suitable physiological parameter that responds to a patient-initiated effort, such as those listed above. The physiological parameter may be estimated, measured, or calculated from an output from one or more sensors 107.

The SDT module 118 evaluates the parameter signal to determine if distortion is present. In an embodiment, the SDT module uses a signal energy approach that assesses the signal's residual value and signal to noise ratio (SNR) to identify signal distortion occurring within a stable signal period. In other embodiments, the SDT module uses other methods to detect distortion, including pattern recognition, phase analysis, spectrum analysis (frequency domain), morphology metrics, multiple/high-order derivatives, signal energy, signal to noise ratio, path length, other similar approaches, or combinations of these.

Figure 4:
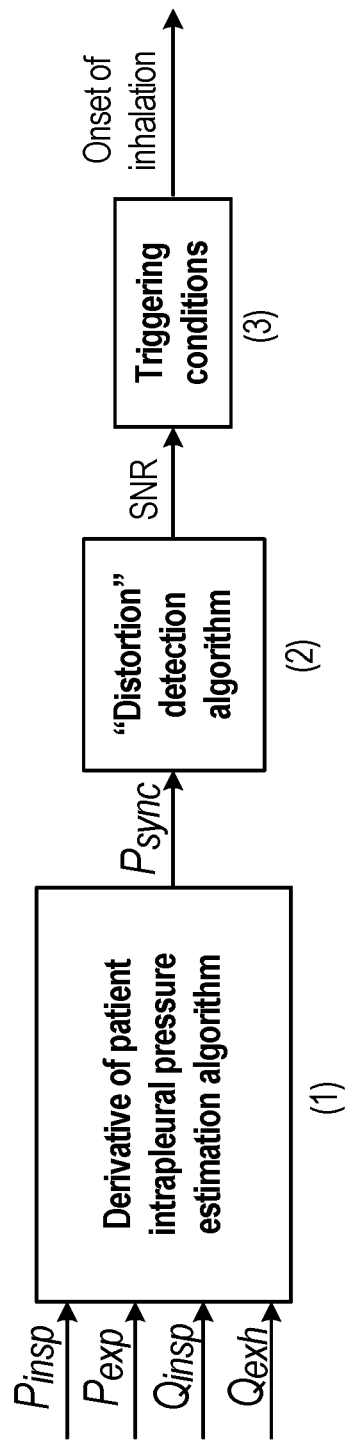
FIG. 4 is a schematic diagram of a signal distortion tracking system, in accordance with aspects of the disclosure.
Figure 5:
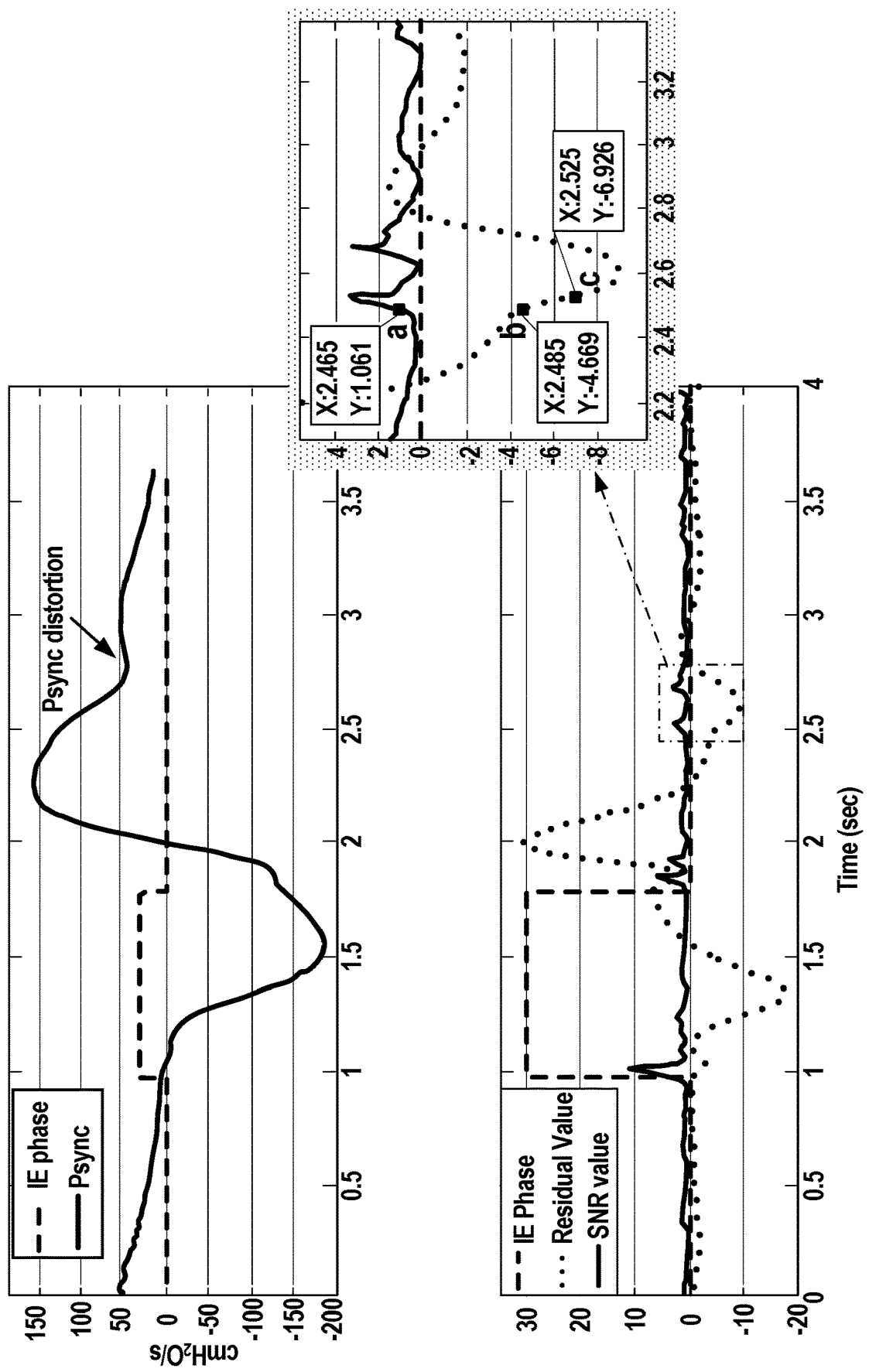
FIG. 5 is a set of charts illustrating trigger detection during ventilation of a patient with a ventilator based on signal distortion tracking, in accordance with aspects of the disclosure.
Figure 6:
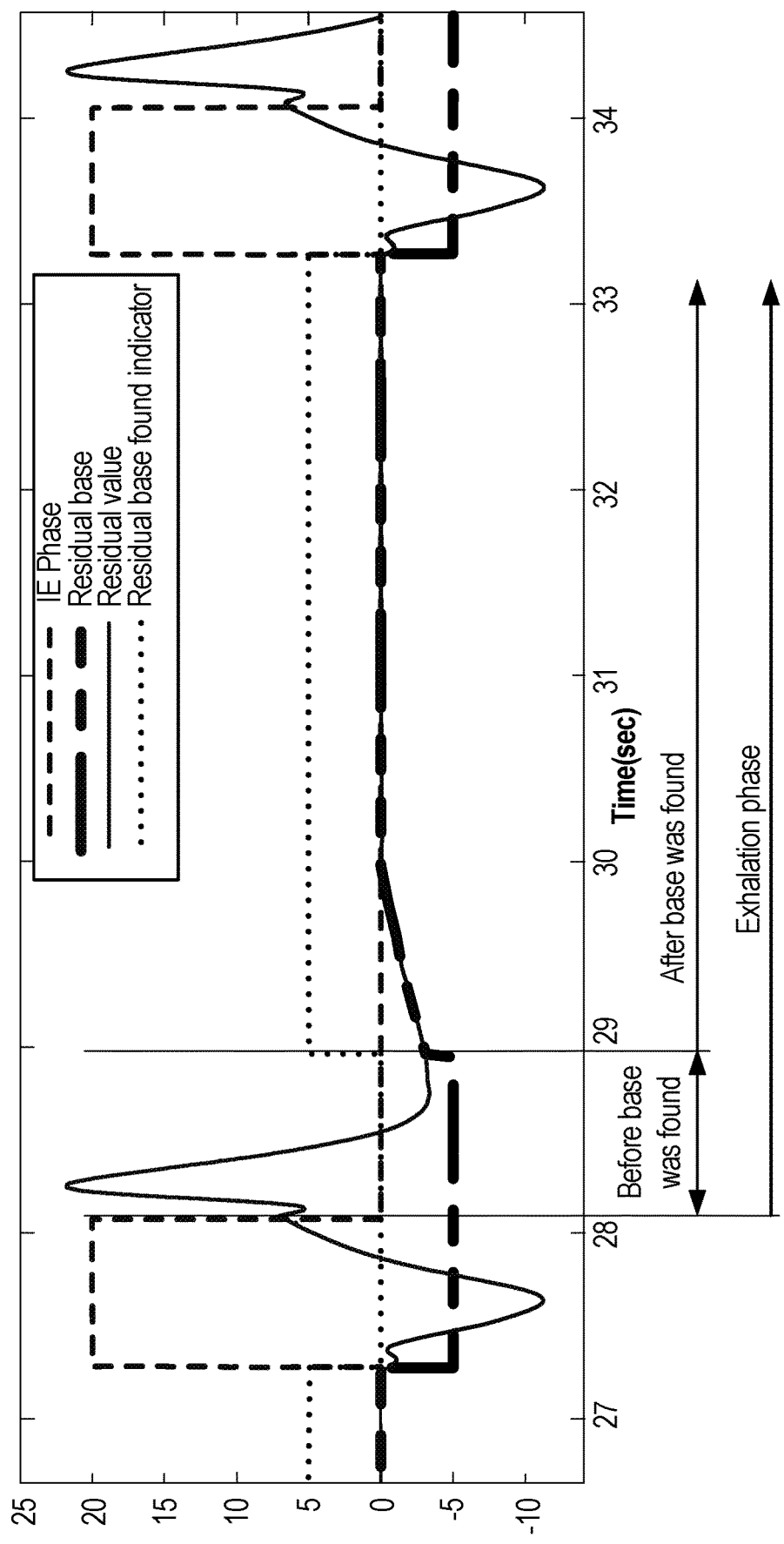
FIG. 6 is a chart illustrating trigger detection during ventilation of a patient with a ventilator based on signal distortion tracking, in accordance with aspects of the disclosure.

In an embodiment, the SDT module 118 evaluates the signal with a distortion detection algorithm based on signal energy, as shown in FIGS. 4-6. In this embodiment, the parameter signal shown is Psync, but flow, pressure, or others can be used with this method. The SDT module 118 receives Psync as the parameter signal and analyzes and tracks a measure of signal energy to identify distortion in the Pysnc signal. When distortion is detected, the SDT module applies a set of triggering conditions to determine whether to trigger inhalation. In an embodiment, the signal energy metric is a residual value of the signal. The deviation of the residual value from a base value (a residual base, example given below) is an indicator of distortion. The triggering condition is satisfied when the deviation is large enough (based on the triggering sensitivity). An example method based on this approach will now be described in more detail.

In the embodiment of FIGS. 4-6, the SDT module 118 checks each current measurement of the physiological parameter (here, Psync) to determine a residual value, a residual base, and an SNR. Signal distortion is identified when a current Psync residual value drops below the residual base. The term "current" as utilized herein refers to the most recently taken, measured, or obtained sample or the one currently being analyzed. The term "next" as utilized herein refers to one or more items that occur immediately after the current item or time.

In an embodiment, the residual value of a current measurement ($X_{res}(n)$) of a physiological parameter signal is the difference between the current measurement and an averaged value of a defined number of the most recently received measurements ($X(n)$) of the signal (a running average). If a signal is flat, the residual value will be near zero, as the current signal value does not differ much from the previous average. If a signal has a stable (nearly constant) slope, the residual value will have a stable non-zero value (as each new signal value differs from the running average by about the same amount). By contrast, when a signal distorts from a stable shape, the residual value increases or decreases, as the new signal value differs uncharacteristically from the previous average. Accordingly, distortion can be detected from changes in the residual value.

In an embodiment, distortion is detected by an increase in a signal-to-noise ratio, and triggering conditions are satisfied based on comparison of the residual value to a residual base. When each new sample of the signal is received, the distortion tracking algorithm calculates a residual value and SNR. If the SNR increases above a threshold, indicating distortion, then the residual base is set to the current residual value. Thereafter, if the next calculated residual value falls below the residual base by a set amount, the triggering condition is satisfied. This approach is shown schematically in FIG. 4, where sensor signals are received into box (1) and processed into a patient parameter signal (in this case Psync). The Psync signal is passed into the distortion detection algorithm in box (2), and the SNR (and/or other distortion metrics) are passed to triggering conditions at box (3). If the triggering conditions are satisfied, then the ventilator initiates inhalation.

A specific example is shown in FIG. 5. In FIG. 5, two graphs illustrate an example of trigger detection during $P_{sync}$ triggering of a patient utilizing a signal distortion triggering method and a $P_{sync}$ signal, in accordance with aspects of the disclosure. In the lower graph of the FIG. 5, the dotted line represents the residual value of the $P_{sync}$ signal and the solid black line represents the SNR value of the $P_{sync}$ signal. The dashed line in both the upper and lower graph in FIG. 5 represents the IE breath phase or, in other words, shows the inhalation (dashed line raised) and exhalation (dashed line lowered) of the patient during $P_{sync}$ triggering. The solid line in the upper graph of FIG. 5 illustrates the $P_{sync}$ signal (which is a graph of the $P_{sync}$ signal versus time).

In this example, during exhalation, when the patient demands inhalation, the Psync signal becomes distorted and dips downward toward the baseline, but does not cross the baseline. In this example, the distortion triggering method triggers inhalation before the patient parameter signal returns to a conventional trigger baseline. In this example, the patient requests a new breath before fully exhaling, and the distortion triggering method responds quickly and triggers a new inhalation. In this example, the distortion triggering method is able to trigger a new breath for the patient even in air trapping conditions, such as when the delivered volume exceeds the exhaled volume.

At point a, which is shown in a zoomed out section of the lower graph in FIG. 5, the SNR value rises above a distortion threshold (for example, 1.05), which means a "distortion" in the $P_{sync}$ signal is detected. In this case, the SNR, or the increase in SNR, is a distortion indicator. As discussed above, a patient's request for inhalation causes a distortion in a physiological patient parameter signal. After distortion is detected, triggering conditions are checked to determine if the ventilator will trigger a new breath. In this case, the triggering conditions are based on a comparison of the residual value to a residual base. Based the distortion detection, the residual base is determined or set to the current value of the residual value, which is −4.669 cmH$_2$O/s (as shown in point b). The ventilator monitors the next residual values of the $P_{sync}$ signal until a difference between the residual base and a current residual value is greater than the set trigger sensitivity, which 2 cmH$_2$O/s in this example. As such, the ventilator triggers a new inspiration at point c where the residual value drops below the residual base by the sensitivity value of 2 cmH$_2$O. For example, the difference between −4.669 cmH$_2$O/s at point b and −6.928 cmH$_2$O/s at point c is 2.259 cmH$_2$O/s, which is greater than 2 cmH$_2$O/s.

The SNR compares the strength/energy of a residual value of a current signal measurement ($X_{res}$(n)) to the strength/energy of the background noise floor. When the SNR for a given measurement is greater than 1 (i.e. greater than 0 dB), it implies that the signal distortion has occurred, since residual value of a current signal measurement ($X_{res}$(n)) overwhelms the background noise floor. (An SNR of about 1 means signal energy is about equal to noise energy, so no detectable distortion.) As such, the SNR may be calculated by dividing a standard deviation of the residual value of the current measurement ($\sigma_{res}$(n)) by the standard deviation of the noise floor of the signal ($\sigma_{noise}$). The standard deviation of the noise floor of the signal ($\sigma_{noise}$) is a median of a defined number of the most recently calculated standard deviations of the most recently determined residual values. The equations below provide examples of how the SNR for a current measurement may be calculated:

$$x_{res}(n) = x(n) - \frac{1}{10} \cdot \sum_{j=n-9}^{n} x(j) \quad (EQ\#1)$$

$$\sigma_{res}(n) = \sqrt{\frac{\sum_{j=n-9}^{n}\left(x_{res}(j) - \frac{1}{10}\sum_{j=n-9}^{n} x_{res}(j)\right)^2}{9}} \quad (EQ\#2)$$

$$SNR(n) = \frac{\sigma_{res}(n)}{\sigma_{noise}} \quad (EQ\#4)$$

$$\sigma_{noise} = \text{median of } \{\sigma_{res}(n-14), \sigma_{res}(n-13), \cdots, \sigma_{res}(n-4)\}, \quad (EQ\#3)$$

where:
  n is the current sample number;
  j is the index of summation;
  X(n) is a current physiological parameter measurement;
  $X_{res}$ (n) is a residual value of a current measurement (or average a defined number of the most recently measurements of the physiological parameter);
  $\sigma_{res}$ (n) is a standard deviation of the residual value of the current measurement; and
  $\sigma_{noise}$ is a standard deviation of the noise floor of the signal (or a median of a defined number of the most recently measurements of the physiological parameter).

In the example equations listed above, the average, standard deviation, and median are all taken from the 10 most recently received measurements of the physiological signal. This is exemplary only and is not meant to be limiting. Any selected number of or the most recent measurements may be utilized by the SDT module 118. For example, in some aspects, the average, standard deviation, and median are taken from the 3, 4, 5, 6, 7, 8, 9, 10, 11, 12, 13, 14, 15, 16, 17, 18, 19, or 20 or other number of most recently received measurements of the physiological signal by the SDT module 118. In some aspects, the number of measurements is equivalent to the number of sample periods or most recently received measurements required to find the residual value of a current measurement ($X_{res}$(n)), the standard deviation of the residual value of the current measurement ($\sigma_{res}$(n)), and/or the standard deviation of the noise floor of the signal ($\sigma_{noise}$).

To employ this method, the SDT module 118 determines a current residual value ($X_{res}$(n)) of a current received sensor measurement. The current residual value is the residual value of a current sensor measurement taken after the determination of the residual base. Next, the SDT module 118 compares the residual base and the current residual value to a trigger sensitivity. In some aspects, the current residual value is subtracted from the residual base and the resulting difference is compared to the trigger sensitivity or trigger threshold. For instance, Equation #4 below provides an example of how the SDT module 118 determines if a trigger sensitivity has been met:

$$\text{residual}_{base} - x_{res}(n) \geq \text{triggering}_{sensitivity} \quad (EQ\#4)$$

where
  residual$_{base}$ is the residual value of the physiological parameter where signal distortion was detected; and
  triggering$_{sensitivity}$ is a change in the residual value of the physiological parameter that must be met for the ventilator to end exhalation and start inhalation.

The trigger sensitivity will vary depending upon the monitored physiological parameter. For example, if the physiological parameter is flow, the trigger sensitivity may be set anywhere from 0.1 to 20 lpm. In another example, if the physiological parameter is pressure, the trigger sensitivity may be set anywhere from 0.1 to 10 cmH$_2$O. In a further example, if the physiological parameter is $P_{sync}$, the trigger sensitivity may be set anywhere from 0.5 to 3.5 cmH$_2$O/s. The provided trigger sensitivities above are exemplary only and are not meant to be limiting. Any suitable triggering threshold for physiological parameter may be utilized by the SDT module 118. In some aspects, the triggering threshold and/or the physiological parameter are defined and/or set automatically by the ventilator. In other aspects, the triggering threshold and/or the physiological parameter are selected and/or set based on user input or selections.

Another example set of waveforms is shown in FIG. 6. FIG. 6 shows breath phase (raised line during inhalation, lowered during exhalation), residual base, and residual value, according to an embodiment. During an initial portion of exhalation, the residual base is set to a low value to prevent auto-triggering (false triggering during exhalation when the patient is not requesting a new breath, such as early in exhalation when it is too soon for the patient to request a new breath). For example, the initial sample period may be a set number of data points of the monitored parameter signal that occur during an initial portion of the exhalation phase, such as immediately after the start or initiation of exhalation, or it may be a set time period (such as 200 ms). During this initial period (also referred to as the first sample period), the residual base is set to a sufficiently low value to prevent triggering, or the residual value may not be calculated at all, the residual value may be set to a fixed value, or triggering may be inactive or prevented.

After that initial period, the SDT module 118 begins searching for a residual base, which will be used to assess whether the residual value is changing uncharacteristically (indicating distortion). In the next sample period (a second sample period following the initial/first sample period), the residual base is calculated dynamically as the residual value is changing. This is shown in FIG. 6 between about 20 and about 30 seconds in the graph. In this portion of the graph, the Psync signal may be falling as the patient's muscle pressure during exhalation falls to zero. Once the Pysnc signal flattens (as the patient ends active exhalation), the residual value becomes about zero, because each new Psync value does not differ much from the previous average.

In an embodiment, the residual base is set to the current value of the residual value if the SNR passes a threshold that indicates distortion. For example, when the signal to noise ratio (SNR) of a residual value of the measurement is greater than or equal to one or about one (e.g., 0.95, 0.96, 0.97, 0.98, 0.99, 1, 1.01, 1.02, 1.03, 1.04, 1.05, 1.06, 1.07, 1.08, 1.09, or 1.1), the SDT module 118 sets the residual base. As such, the residual base is equivalent to a residual value of the last measurement or last value of the signal (or physiological patient parameter) just before or at the beginning of the distortion. Thereafter, if the next residual value falls below that residual base by a set amount (the sensitivity), the ventilator will trigger a new inspiration. In this scenario, the residual base is a residual value of the signal at a time of signal distortion. For example, referring again to FIG. 6, the residual value drops below the residual base after 33 seconds, just before the ventilation triggers a new inhalation.

Accordingly, in certain embodiments, a signal energy approach is used to detect distortion in a signal and apply triggering conditions. In the example above, the SNR crossing a noise threshold is an indicator of distortion in the signal. Other distortion indicators may be used in the alternative or in addition to the SNR. For example, one, two, three, or more different metrics could be used in combination to determine that distortion is present. When distortion is present, the SDT module applies triggering conditions to determine if the ventilator will trigger a new breath. In the example above, the triggering conditions are satisfied when the deviation of a residual value below a residual base passes a sensitivity threshold. Other triggering conditions may be used in the alternative or in addition to the deviation of the residual value. The triggering conditions act as a filter on the distortion indicator to filter out small distortions that are not necessarily indicative of a patient effort to breathe, and pass through larger distortions that are indicative of patient effort.

If the SDT module 118 determines that the trigger sensitivity has not been met, then the SDT module 118 waits for the next measurement for the next sample period. Further, in some aspects, if the SDT module 118 determines that trigger sensitivity has not been met, the SDT module 118 does not send any information to the inspiratory module 104. In other aspects, if the SDT module 118 determines that the trigger sensitivity has not been met, the SDT module 118 determines a second result. The second result may be instructions and/or a command to not trigger inspiration or to continue exhalation. In other aspects, the second results may be a notification that the trigger sensitivity has not been met. In some aspects, if the SDT module 118 receives or determines a second result, the ventilator continues to deliver exhalation until the SDT module 118 receives and evaluates a another sample period (or until an apnea interval is triggered, as defined below).

In an embodiment, if the SDT module 118 determines that the trigger sensitivity has been met, the SDT module 118 sends a first result to the inspiratory module 104. The first result may be instructions and/or a command to trigger inspiration and/or to end expiration. In alternative aspects, the first result may be a notification that the trigger sensitivity has been met. In other aspects, the SDT module 118 sends the first or second result to any suitable component or module of the ventilator 100, such as the pneumatic system 102, expiratory module 108, inspiratory module 104, processor 116, controller 110, and/or etc. Additional examples of actions taken after a determination that distortion is or is not present are given below.

To prevent apnea in the event that a patient trigger is not detected for a long duration by the SDT mode of the ventilator 100, the SDT module 118 also triggers inspiration after a defined amount exhalation time. The defined amount of exhalation time is also known as an apnea interval in some ventilators. For example, the SDT module 118 (or other component of the ventilator) will automatically trigger an inspiration after 20 seconds, 30 seconds, or 60 seconds of exhalation time. In some aspects, the apnea interval time is determined by the clinician and/or ventilator 100 based on whether the patient 150 is an infant, child, adult, male, female, and/or suffering from a specific disease state.

The SDT module 118 triggers inspiration by sending instructions and/or a command to a pneumatic system 102, an expiratory module 108, an inspiratory module 104, a processor 116, and/or a controller 110. The instructions and/or commands cause the one or more ventilator components and/or modules to change the delivered flow and/or pressure and to adjust the valves as needed to trigger inspiration.

As described above, a signal energy approach is used to detect distortion in a signal when a calculated SNR exceeds a threshold (indicating distortion is present) and a residual value deviates below a residual base by a defined amount (satisfying the triggering conditions). Other methods of detecting signal distortion to trigger inhalation may be used in addition or alternatively to a residual base analysis. Methods include pattern recognition, spectrum analysis (frequency domain), morphology metrics, multiple/high-order derivatives, signal energy, signal to noise ratio, path length, other similar approaches, or combinations of these.

According to an embodiment, a ventilator includes a signal distortion tracking system that monitors signal distortion of a monitored patient parameter to detect patient cycling efforts (efforts to end inhalation and cycle to exhalation) and/or to determine if the set cycling threshold is appropriate for the patient. According to an embodiment, the SDT module 118 monitors a physiological parameter of the patient to identify when a distortion due to patient effort is present in the signal. The physiological parameter may be any suitable physiological parameter that responds to a patient initiated effort, such as those listed above.

In embodiments described herein, the ventilator effectively identifies the end of patient inspiratory effort and determines the time to cycle into the expiratory phase. Based on this approach, cycling to the expiratory phase will be variable based on patient effort and will not be purely dependent upon exhaled flow (or other parameter) returning to a baseline. Monitoring of the distortion indicator to detect cycling reduces patient-to-ventilator asynchrony and is easy to use for clinicians, since the clinician do not have to actively determine a proper cycling setting.

The SDT module 118 processes the physiological parameter to detect patient cycling efforts. In some aspects, the SDT module 118 processes the physiological parameter to determine a distortion of the physiological parameter to detect patient cycling efforts. The SDT module 118 calculates the distortion of a physiological parameter by inputting a measured physiological parameter from a sensor (such as flow or pressure) into a distortion algorithm. The distortion algorithm takes into account signal noise and other factors. In an embodiment, distortion of a signal is determined according to the signal energy approach described above for triggering. As described above for triggering, the same approach can be used during inhalation phase to detect cycling, by detecting distortion in a signal when (i) a residual value deviates below a residual base by a defined amount and (ii) a calculated SNR exceeds a defined threshold.

In an embodiment, the distortion of a signal x(n) can be determined by the equations provided below:

$$\begin{cases} SNR(n) = \dfrac{\sigma_{res}(n)}{\sigma_{noise}} \\ \sigma_{res}(n) = \sqrt{\dfrac{\sum_{j=n-9}^{n}\left(x_{res}(j) - \frac{1}{10}\sum_{j=n-9}^{n}x_{res}(j)\right)^2}{9}} \\ x_{res}(n) = x(n) - \dfrac{1}{10}\cdot\sum_{j=n-9}^{n}x(j) \\ \sigma_{noise} = \text{median of } \{\sigma_{res}(n-14), \sigma_{res}(n-13), \cdots, \sigma_{res}(n-4)\} \end{cases}$$

These equations are exemplary only and not meant to be limiting. Any suitable algorithm for determining the distortion of a signal may be utilized. Other methods of detecting signal distortion to cycle to exhalation may be used in addition or alternatively to a residual base analysis. Methods include pattern recognition, spectrum analysis (frequency domain), morphology metrics, multiple/high-order derivatives, signal energy, signal to noise ratio, path length, other similar approaches, or combinations of these.

Figure 7:
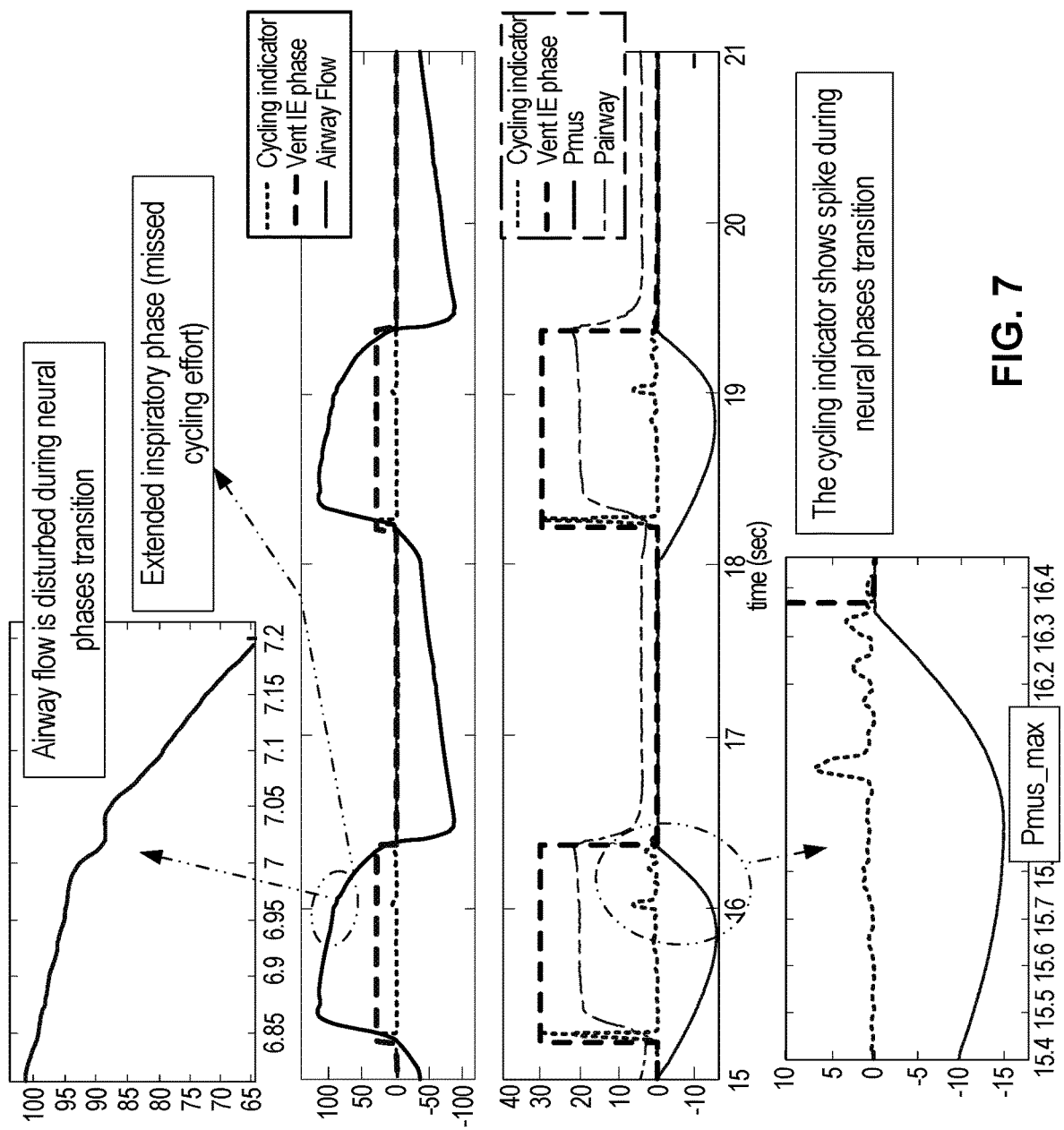
FIG. 7 is a set of charts illustrating cycle detection during ventilation of a patient with a ventilator based on signal distortion tracking, in accordance with aspects of the disclosure.

A distortion tracking approach according to an embodiment is illustrated in FIG. 7. In this embodiment, the distortion algorithm processes each physiological parameter measurement and outputs a distortion indicator. The distortion algorithm detects the onset of patient's neural expiratory phase by identifying the airway flow characteristics when the patient's diaphragmatic muscle effort transits from neural inspiratory phase to neural expiratory phase.

The SDT module 118 compares the distortion indicator to a distortion threshold to form a comparison. If the distortion indicator meets the distortion threshold based on the comparison, the SDT module 118 determines that the patient is making an effort to end inhalation and start exhalation. If the distortion indicator does not meet the distortion threshold based on the comparison, the SDT module 118 determines that the patient is not making an effort to end inhalation and start exhalation. In response to determining that the patient is not making an effort to end inhalation and start exhalation, the SDT module 118 continues to the monitor the signal distortion and compare it to the distortion threshold. The distortion threshold may be dynamic and dependent on the noise level in the system which includes patient and ventilator.

The Pmus signal (shown at the bottom of FIG. 7) is a measurement or estimation of a patient's diaphragmatic muscle effort. When the patient's diaphragmatic muscle effort transits from neural inspiration into neural expiration, the airway flow (also plotted in FIG. 7) is disturbed, which can be identified by the proposed distortion algorithm by generating a distortion indicator (also plotted in FIG. 7). As shown in FIG. 7, the spike on the distortion indicator (also referred to as a cycling indicator) during the inspiratory phase reveals that the airway flow is disturbed by the transition of neural phases, and the neural expiration starts. Physiologically, the cessation of Pmus is not instantaneous after the end of neural inspiration TI, where the diaphragmatic muscle effort Pmus reaches its maximum value $Pmus\_max$. Rather, the muscle activity generally extends into expiratory phase, resulting in residual Pmus during neural expiration, where the Pmus is generally considered to decline exponentially with a time constant of neural expiratory phase.

Actions Performed

Based on the distortion analysis described above, the ventilator performs one or more actions. The action may include triggering inhalation, cycling to exhalation, recommending an adjustment to or automatically adjusting a sensitivity setting, recommending an adjustment to or automatically adjusting another ventilator setting, recommending or automatically transitioning to a different breath type or mode, determining or displaying a notification of asynchrony, displaying a detected patient effort, providing a notification, and/or providing a recommendation.

In some aspects, the one or more actions may include sending a command to end inspiration and begin exhalation, or to end exhalation and begin inhalation. The SDT module 118 ends inspiration or exhalation by sending instructions and/or a command to a pneumatic system 102, an expiratory module 108, an inspiratory module 104, a processor 116, and/or a controller 110. The instructions and/or commands cause the one or more ventilator components and/or modules to change the delivered flow and/or pressure and to adjust the valves as needed to end inspiration and start exhalation, or to end exhalation and start inhalation.

By analyzing signal distortion to initiate a trigger or cycle, the ventilator can adapt to varying patient conditions. The spontaneous breath types adjust to trigger or cycle in response meeting a variable distortion threshold. In these aspects, the ventilator effectively identifies an optimal time to cycle or trigger in each breath. Based on this approach, triggering to inspiratory phase or cycling to the expiratory phase will be variable based on patient effort and will not be purely dependent upon measured flow (or other parameter). The SDT module 118 reduces the patient-to-ventilator asynchrony and provides a feature that is easy to use by the clinician since the clinician does not have to continually adjust sensitivity settings to adapt breath-to-breath.

In an embodiment, the one or more actions includes automatically adjusting (or recommending adjustment of) a sensitivity of a trigger or cycle detection. Trigger sensitivity and cycle sensitivity describe the extent of deviation that is needed before the ventilator will initiate a trigger (start an inhalation) or cycle (end an inhalation). Traditionally inspiration is triggered based on a trigger sensitivity setting (such as an Isens threshold) and inspiration is cycled off based on a cycle sensitivity setting (such as an Esens threshold), which may be a set percentage (normally 25%) of the peak inspiratory flow or a set flow value on many intensive care ventilators. This adjustable value, however, is often not optimal, resulting in patient-ventilator asynchrony.

Both inspiratory asynchrony and expiratory asynchrony have been shown to be problematic in the patients with partial ventilatory support. For example, under the expiratory asynchrony situation, the termination of the ventilator flow occurs either before or after patients stop their inspiratory efforts. When the termination of the ventilator flow falls behind the end of the patient inspiratory effort (i.e. delayed cycling), the patient recruits his or her expiratory muscles to "fight" against the ventilator flow, which increases expiratory workload, resulting in intrinsic PEEP. When the termination of the ventilator flow occurs before the end of patient inspiratory effort (i.e. premature cycling), the patient inspiratory muscle work continues into or even throughout the ventilator's expiratory phase, thus resulting in inefficient inspiratory muscle work. Furthermore, a high lung volume caused by the previous breath with delayed cycling may result in a missed trigger of the subsequent inspiratory effort in patients with Chronic Obstructive Pulmonary Disease (COPD) or with high breathing rates. For patients ventilated with pressure support (PS) ventilation, premature cycling may result in double-triggering or auto-triggering.

Many ventilators in the current market allow the user to select an expiratory cycling setting from a specific range provided by the ventilator. Unlike universal settings such as respiratory rate, PEEP, tidal volume, and pressure support, the expiratory cycling settings are unique to each ventilator. Users who are unfamiliar with a specific ventilator outside their daily use may struggle to properly set the expiratory cycling settings. Moreover, patients need different adjustments when their recovery conditions have changed, or their sedation and pain medications are adjusted. But many clinicians do not adjust the settings optimally to support patient effort.

For example, for cycling to exhalation in pressures support (PS) or volume support (VS) ventilation (cycling), the exhalation sensitivity (ESENS) setting is frequently left at the default value (25%), which can cause asynchrony in some types of patients. For example, with COPD patients, this value can lead to the patient fighting the ventilator trying to exhale. In proportional assist (PA) ventilation, the exhalation sensitivity (ESENS) setting is also frequently left at a default value (such as 3.0 Lpm), which can cause asynchrony in some types of patients. Further, in proportional assist (PA) ventilation, if the percent support setting (k) is set too high, the patient can be over-supported leading to the patient forcing the exhalation mid-way through inspiration. Having the ventilator identify this over-support condition could give the ventilator the ability to detect the patient fighting the ventilator to exhale, not just in PA, but in PS/VS as well. The exhalation issues contribute to poor synchrony.

Accordingly, in an embodiment, the signal distortion tracking system can be used in a monitoring mode to adjust trigger or cycling sensitivity settings for PS, PA, and VS breath types to improve ventilator cycling or to adjust the percent support setting for PA breath type to improve ventilator-patient synchrony. In this example, the SDT module does not actively provide triggering or cycling commands to the ventilator, but instead monitors the patient parameter signal to identify instances when the ventilator missed a patient effort. The ventilator delivers breaths in a different trigger mode such as pressure, flow, or Psync returning to a baseline. The SDT module in monitoring mode can suggest adjusted triggering or cycling settings that may reduce the occurrence of asynchrony and require less operator training or knowledge for effective use. In some aspects, the triggering or cycling setting improves ventilator synchrony by changing the triggering or cycling threshold or recommending a change in threshold based on the monitoring of signal distortion of a monitored patient parameter.

In an embodiment, in monitoring mode, the one or more actions may include determining if exhalation (or inhalation) was provided by the ventilator within an interval of time of a detected cycling (or triggering) effort. In these aspects, cycling/triggering is still controlled by ESENS in PS,VS and PA or other breath modes. As such, the SDT module 118 determines if the detected cycling/triggering effort occurred within a defined amount of time of the breath delivered by the spontaneous breath mode. In some aspects, the interval of time may be about 300 ms. If the ventilator response (triggering or cycline) is not within 300 ms (or other time interval) of the detected patient effort, the SDT module 118 determines asynchronous cycling/triggering. In response to determining asynchrony, the SDT module 118 may provide a notification (such as a notification of an asynchronous cycling or triggering), provide a recommendation (such as a recommendation to adjust ESENS or ISENS for a VS, PS or PA breath type or percent support setting for PA breath type), automatically adjust a ventilator setting (such as automatically adjust ESENS or ISENS for a VS, PS or PA breath type or percent support setting for PA breath type).

In other aspects, the one or more actions include displaying the detected patient effort and/or the distortion indicator. In some aspects, the detected patient effort may be displayed on waveform. In an embodiment, the distortion indicator is displayed versus time on a graph, and may be displayed along with a pressure or flow waveform (or both, or other parameter waveforms) (see, for example, FIGS. 5, 6, and 7). In other aspects, a visual or audible prompt may indicate that a patient effort was detected and/or missed. In an embodiment, the one or more actions include displaying a synchrony or asynchrony index.

In further aspects, the one or more actions may include providing, such as displaying, a recommendation to change a percent support setting in PA or a sensitivity setting in PS,VS or PA as discussed above. In further aspects, the one or more actions may include automatically changing a percent support setting in PA or a sensitivity setting in PS, VS or PA. For example, if a detected patient effort to cycle happens before exhalation was delivered, the SDT module 118 may recommend increasing (or automatically increase) the sensitivity or recommend decreasing (or automatically decrease) the percent support setting. If the detected effort to cycle happens after exhalation was delivered, the SDT module 118 may recommend decreasing (or automatically decrease) the sensitivity or recommend increasing (or automatically increase) the percent support setting.

In an embodiment, the one or more actions include displaying waveforms, parameters, indicators, metrics or combinations of these to help a clinician manually adjust pressure, flow, and sensitivity settings.

Additional aspects of the ventilator 100 are described below, with reference to FIG. 3. Ventilation tubing system 130 (or patient circuit 130) may be a two-limb as shown (or a one-limb) circuit for carrying gases to and from (or only to) the patient 150. In a two-limb aspect, a fitting, typically referred to as a "wye-fitting" 170, may be provided to couple the patient interface 180 (shown as an endotracheal tube in FIG. 3) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106, accumulator and/or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 controls an inspiratory valve to deliver gases to the patient 150 through the inspiratory limb 132 according to prescribed ventilatory settings and modes, such as mandatory, spontaneous, and/or assist modes. The expiratory module 108 controls an expiratory valve to release gases from the patient's lungs according to prescribed ventilatory settings and modes, such as mandatory, spontaneous, and/or assist modes.

The sensors 107 may be located in the pneumatic system 102, in an accumulator, in or affixed to ventilation tubing system 130 or the wye 170, in components or modules of the ventilator 100, and/or on the patient 150. For example, sensors 107 may be coupled to the inspiratory module 104 and/or expiratory module 108 for detecting changes in, for example, circuit pressure and/or flow. FIG. 3 illustrates a sensor 107 (e.g., flow sensor, pressure sensor, etc.) in pneumatic system 102. Sensors 107 may generate output, such as measurements, and send this output to (and communicate with) various components of ventilator 100, e.g., pneumatic system 102, other sensors 107, expiratory module 108, inspiratory module 104, processor 116, controller 110, signal distortion trigger (SDT) module 118, and any other suitable components and/or modules. For example, in some aspects, the one or more sensors 107 of the ventilator 100 include an inspiratory flow sensor and an expiratory flow sensor. Ventilatory parameters may be directly monitored by one or more sensors 107, as described above, or may be indirectly monitored or estimated by derivation according to the Equation of Motion or other known relationships from the monitored parameters.

The pneumatic system 102 may include a variety of other components, including mixing modules, valves, tubing, accumulators, filters, etc. Controller 110 is operatively coupled with pneumatic system 102, signal measurement and acquisition systems (e.g., sensor(s) 107), and an operator interface 120 that may enable an operator to interact with the ventilator 100 (e.g., change ventilator settings, select operational modes, view monitored parameters, etc.). In some aspects, the operator interface 120 of the ventilator 100 includes a display 122 communicatively coupled to ventilator 100. Display 122 may provide various input screens, for receiving clinician input, and various display screens, for presenting useful information to the clinician. In aspects, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some aspects, the display 122 illustrates a physiological parameter, a graph or waveform of the physiological parameter, a detected patient trigger, a trigger sensitivity, use of SDT type, and/or any other information known, received, or stored by the ventilator 100.

In some aspects, controller 110 includes memory 112, one or more processors 116, storage 114, and/or other components of the type commonly found in command and control computing devices. Controller 110 may further include the signal distortion trigger module 118 as illustrated in FIG. 3. In alternative aspects, the signal distortion trigger module 118 is located in other components of the ventilator 100, such as in the pressure generating system 102 (also known as the pneumatic system 102) or inspiratory module 104.

The memory 112 includes non-transitory, computer-readable storage media that stores and/or encodes software (or computer readable instructions) that is executed by the processor 116 and which controls the operation of the ventilator 100. In an aspect, the memory 112 includes one or more solid-state storage devices such as flash memory chips. In an alternative aspect, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Figure 8:
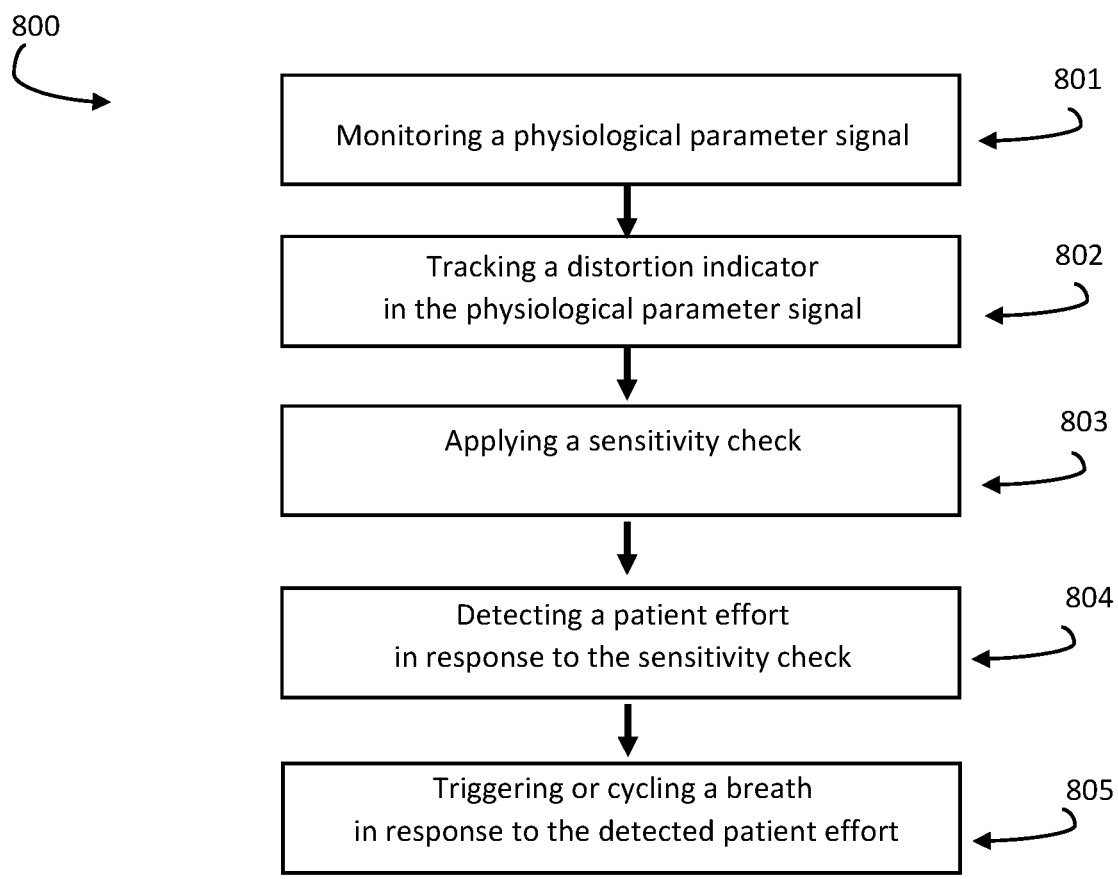
FIG. 8 is a flow diagram illustrating a method for signal distortion triggering/cycling in a spontaneous breath type during ventilation of a patient with a ventilator, in accordance with aspects of the disclosure.
Figure 9:
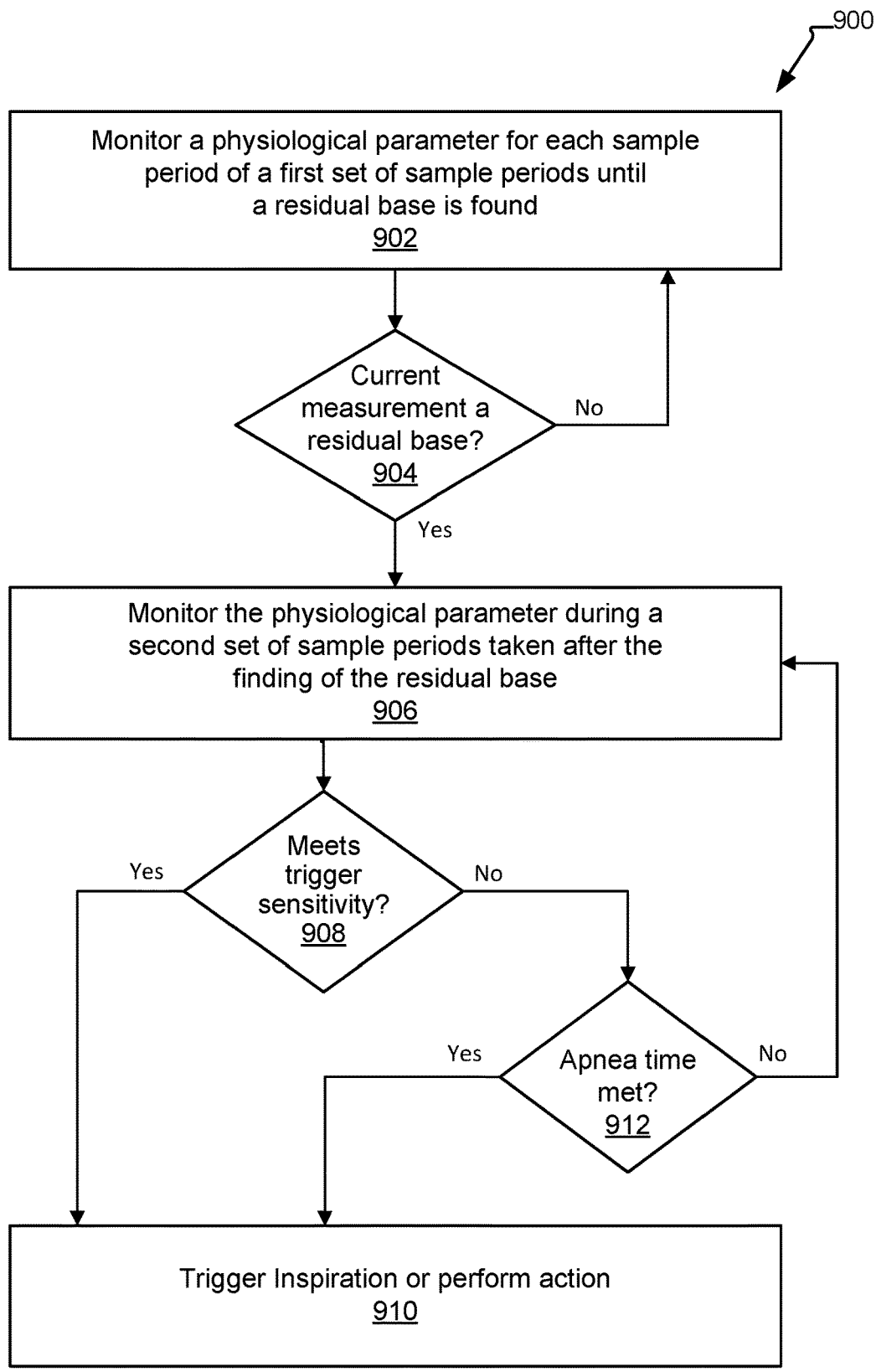
FIG. 9 is a flow diagram illustrating a method for signal distortion triggering in a spontaneous breath type during ventilation of a patient with a ventilator, in accordance with aspects of the disclosure.
Figure 10:
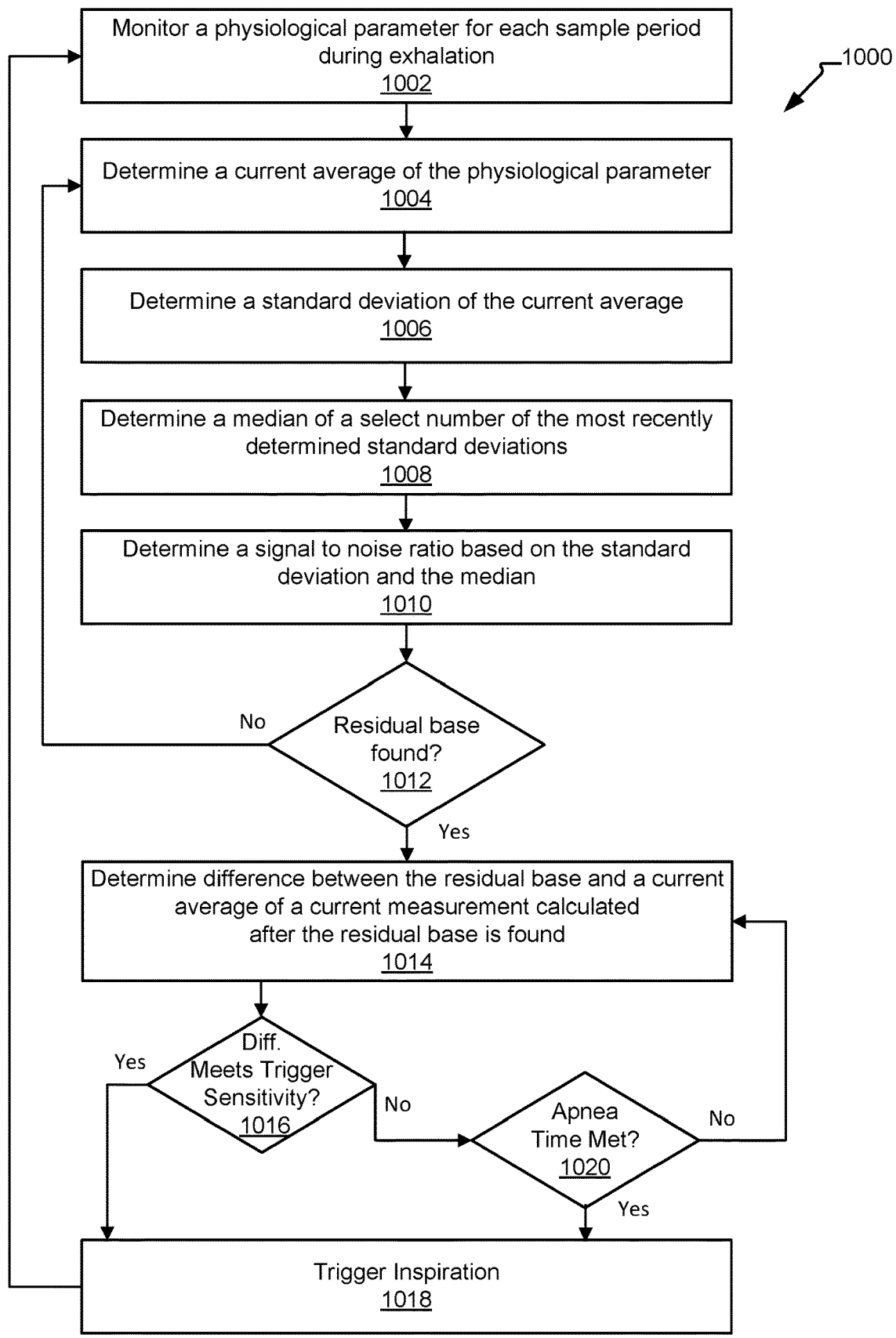
FIG. 10 is a flow diagram illustrating a method for signal distortion triggering in a spontaneous breath type during ventilation of a patient with a ventilator, in accordance with aspects of the disclosure.

Exemplary methods of detecting distortion to perform an action on a ventilator are shown in FIGS. 8-10. An embodiment of a method 800 for triggering or cycling a breath during spontaneous ventilation of a patient on a mechanical ventilator is shown in FIG. 8. The method includes monitoring a physiologic parameter signal of the patient at 801. For triggering, this monitoring is done during an exhalation phase, and for cycling this monitoring is done during the inhalation phase. The method includes tracking a distortion indicator in the physiological parameter signal at 802. For example, the distortion indicator may be a deviation of a residual value of the physiological parameter signal from a residual base, or a deviation of a signal to noise threshold above a noise threshold, or a morphology pattern identified in the physiological parameter signal, or an energy or frequency content of the physiological parameter signal, or other examples or combinations described herein.

The method includes applying a sensitivity check at 803, and detecting a patient effort in response to the sensitivity check at 804. The sensitivity check may be a comparison of the distortion indicator to a threshold or magnitude, to confirm that the distortion is large enough to signify a patient effort. If the distortion indicator satisfies the sensitivity check, then a patient effort is detected. For example, the ventilator may set an effort flag, or generate an effort signal indicating the presence of an effort. The method includes triggering or cycling a breath in response to the detected patient effort at 805.

The method 800 can be utilized during exhalation to trigger a new inhalation, and/or during inhalation to cycle to exhalation. In an embodiment, the same signal distortion method is used for both triggering and cycling, with a first sensitivity check applied to detect a patient effort to inhale and a second different sensitivity check applied to detect a patient effort to exhale. In an embodiment, a first distortion indicator is used for triggering (such as a residual value compared against a residual base), and a second different distortion indicator is used for cycling (such as an SNR crossing a noise threshold).

In an embodiment, the SDT module operates independently of the presence of leak in the ventilation circuit. Other leak compensation systems operate to add flow to a breath to compensate for losses due to leak. The SDT module detects distortions from patient effort, and thus can operate both with or without leak present. The signal distortion approach is applicable to both leak and non-leak scenarios, and both invasive ventilation (such as through an endotracheal tube, nasal/oral tube, laryngeal mask, or tracheostomy tube) and non-invasive ventilation (such as through nasal prongs or a nasal, oral, or face mask).

In an embodiment, a ventilator system includes a pressure generating system that generates a flow of breathing gas, and one or more sensors operatively coupled to at least one of the pressure generating system, a patient, and a ventilation tubing system that delivers the flow of breathing gas from the pressure generating system to the patient. The system also includes at least one processor and a memory for storing and encoding computer-executable instructions. When executed by the at least one processor, the instructions are operative to carry out the method 800.

FIG. 9 illustrates an aspect of a method 900 for triggering inspiration or cycling to exhalation during ventilation of a patient on a ventilator. The method 900 triggers inspiration or cycles to exhalation based on the monitoring of signal distortion or a measured physiological parameter's waveform shape. As such, method 900 provides spontaneous ventilation utilizing an SDT type. According to an embodiment, a method for triggering inspiration (or cycling to exhalation) during spontaneous ventilation of a patient on a ventilator includes monitoring a physiological parameter during exhalation (inhalation) in a first period before identifying a residual base in the physiological parameter signal. The method includes identifying a residual base in the signal when the signal reaches a stable condition. In response to finding the residual base, the method includes monitoring the physiological parameter during exhalation (inhalation) in a second period subsequent to the first period. The method includes, during the second period, dynamically determining a residual value of the signal, comparing the residual value to the residual base, and determining if the comparison meets a trigger sensitivity. The method includes determining that the trigger sensitivity is met based on the comparison, and triggering inspiration (or cycling to exhalation) in response to the determination.

Method 900 begins at the start of spontaneous ventilation utilizing an SDT type. As discussed above, method 900 can detect a patient's attempt to inhale before exhalation has ended. Further as discussed above, method 900 decreases the amount of time needed to detect a patient trigger when compared previously utilized flow triggering, pressure triggering and $P_{sync}$ trigger types that required a comparison to baseline. Method 900 decreases the amount of time needed to detect a patient trigger because method 900 does not have to wait for a signal baseline to occur. As illustrated, method 900 includes a first monitoring operation 902, a residual base detection operation 904, a second monitoring operation 906, a threshold decision operation 908, and a trigger operation 910. In some aspects, method 900 also includes an apnea operation 912.

During the first monitoring operation 902, the ventilator monitors a physiological parameter based on one or more sensor measurements for each sample period in a first set of sample periods during exhalation until a residual base is found. In some aspects, the ventilator during the first monitoring operation 902 monitors flow, pressure, and/or $P_{sync}$. Sensors suitable for this detection may include any suitable sensing device as known by a person of skill in the art for a ventilator, such as an inspiratory flow sensor, inspiratory pressure sensor, an exhalation flow sensor, an exhalation pressure sensor, and/or exhalation auxiliary pressure sensor. In further aspects, the ventilator during the first monitoring operation 902 delivers exhalation.

During the residual base detection operation 904, the ventilator determines if a residual base is present based on a current received sensor measurement of the physiological patient parameter from the first set of sample periods. If the ventilator determines during operation 904 that the residual base is present based on the current received sensor measurement, the ventilator selects to perform second monitoring operation 906. If the ventilator determines during operation 904 that the residual base is not present based on the current received sensor measurement, the ventilator continue to perform monitoring operation 902 and residual base detection operation 904 until a residual base is detected/present or until an apnea time period is met.

In some aspects, the ventilator during residual base detection operation 904, the ventilator sets the residual base to the residual value of physiological parameter signal at the time a distortion of the signal of the physiological parameter is detected. In some aspects, the ventilator during residual base detection operation 904 calculates a signal to noise ratio (SNR) based on the current measurement and compares the SNR to a threshold. In further aspects, the ventilator during residual base detection operation 904 determines a residual value of a current received sensor measurement, a standard deviation of the residual value of the current measurement ($\sigma_{res}(n)$) by the standard deviation of the noise floor of the signal ($\sigma_{noise}$). In some aspects, the ventilator during residual base detection operation 904 determines or calculates the SNR by dividing a standard deviation of the residual value of the current measurement ($\sigma_{res}(n)$) by the standard deviation of the noise floor of the signal ($\sigma_{noise}$). The standard deviation of the noise floor of the signal ($\sigma_{noise}$) is a median of a defined number of the most recently calculated standard deviations of the most recently determined residual values. The residual value of a current measurement ($X_{res}(n)$) is an averaged value of a defined number of the most recently received measurements of the physiological parameter of the patient. In other aspects, the ventilator during residual base detection operation 904 utilizes Equation #1-4 above to determine if the current residual value of the signal is the residual base.

At the second monitoring operation 906, the ventilator monitors the physiological parameter based on a most recently received sensor measurement in a second set of sample periods that occur during the exhalation after the residual base is determined. Next, during threshold decision operation 908, the ventilator determines if a trigger sensitivity has been met based on a comparison of the residual base and the most recently received sensor measurement to a trigger sensitivity. In some aspects, the ventilator during threshold decision operation 908 determines if a trigger sensitivity has been met by comparing a mathematical relationship between the residual base and a residual value of the current received sensor measurement to a trigger sensitivity. In some aspects, the ventilator during threshold decision operation 908 determines if a trigger sensitivity has been met by comparing a difference between the residual base and a residual value of the current received sensor measurement to a trigger sensitivity. In further aspects, the ventilator during threshold decision operation 908 calculates the residual value of the most recently received sensor measurement.

If the ventilator during threshold decision operation 908 determines that the trigger threshold has been met, then the ventilator selects to perform trigger operation 910. In some aspects, if the ventilator during threshold decision operation 908 determines that the trigger threshold has been met, then the ventilator determines a first result based on the comparison. In response to the first comparison result, the ventilator may select to perform trigger operation 910. If the ventilator during threshold decision operation 908 determines that the trigger threshold has not been met, then the ventilator selects to perform apnea operation 912 or continues to perform threshold decision operation 908. In some aspects, if the ventilator during threshold decision operation 908 determines that the trigger threshold has not been met, then the ventilator determines a second result based on the comparison. In response to the second comparison result, the ventilator may select to perform apnea operation 912 or continues to perform threshold decision operation 908.

At trigger operation 910, the ventilator triggers inspiration (and/or cycles to exhalation or performs other actions as described herein). The triggering of inspiration ends the exhalation. During inspiration, the ventilator delivers breathing gas to the patient. In some aspects, the ventilator delivers breathing gas to the patient according a set breath type during inspiration.

As discussed above, in some aspects, method 900 includes an optional apnea operation 912. At apnea operation 912, the ventilator determines if an apnea time period has been met or in other words if exhalation has been going on for too long. If the ventilator determines that the apnea time period has been met during operation 912, the ventilator performs trigger operation 910. If the ventilator determines that the apnea time period has not been met during operation 912, the ventilator again performs threshold decision operation 908.

FIG. 10 illustrates an aspect of a method 1000 for triggering inspiration during ventilation of a patient on a ventilator. Further, the method 1000 triggers ventilation based on the monitoring of signal distortion or a measured physiological parameter's waveform shape. As such, method 1000 provides spontaneous ventilation utilizing a SDT type. The method 1000 begins at the start of spontaneous ventilation utilizing a SDT type. As discussed above, method 1000 can detect a patient's attempt to inhale before exhalation has ended. Further as discussed above, method 1000 decreases the amount of time needed to detect a patient trigger when compared previously utilized flow triggering, pressure triggering and $P_{sync}$ trigger types that required a comparison to baseline. As illustrated, method 1000 includes a monitoring operation 1002, average operation 1004, a standard deviation operation 1006, a median operation 1008, a quotient operation 1010, a residual base decision operation 1012, a difference operation 1014, a trigger threshold decision operation 1016, and an inspiration operation 1018. In some aspects, method 1000 also includes a time operation 1020.

During the monitoring operation 1002, the ventilator monitors a physiological parameter based on one or more sensor measurements for a sample period during exhalation. In some aspects, the ventilator during the monitoring operation 1002 monitors all sample periods during exhalation. In other aspects, the ventilator during the monitoring operation 1002 monitors all sample periods during exhalation after a defined number of initial sample periods have occurred. In some aspects, the ventilator during the monitoring operation 1002 monitors flow, pressure, and/or $P_{sync}$. Sensors suitable for this detection may include any suitable sensing device as known by a person of skill in the art for a ventilator, such as an inspiratory flow sensor, inspiratory pressure sensor, an exhalation flow sensor, an exhalation pressure sensor, and/or exhalation auxiliary pressure sensor. In further aspects, the ventilator during the monitoring operation 1002 delivers exhalation.

During average operation 1004, the ventilator determines or calculates a current average of the measurements from a defined number of most recent sample periods. In some aspects, the ventilator utilizes Equation #1 above to determine the current average of the measurements from the defined number of the most recent sample periods during average operation 1004.

During standard deviation operation 1006, the ventilator determines or calculates a standard deviation of the current average. In some aspects, the ventilator utilizes Equation #2 above to determine the standard deviation of the current average during standard deviation operation 1006.

During median operation 1008, the ventilator determines or calculates a median of a select number of the most recently determined standard deviations. In some aspects, the ventilator utilizes Equation #3 above to determine the median of the select number of the most recently determined standard deviations during standard deviation operation 1006.

While operations 1004, 1006, and 1008 are shown as being performed in a certain order, this sequence is not meant to be limiting. Operations 1004, 1006, and 1008 may be performed in any order, simultaneously, and/or at overlapping times.

Next at quotient operation 1010, the ventilator determines the signal to noise ratio for the current measurement based on the standard deviation of the current signal measurement and the median. In some aspects at quotient operation 1010 the standard deviation of the current signal measurement is divided by the median.

Next at residual base decision operation 1012, the ventilator compares the signal to noise ratio to a defined threshold. If the ventilator determines during operation 1012 that the signal to noise ratio meets the defined threshold, the ventilator selects to perform difference operation 1014. If the ventilator determines during operation 1012 that the signal to noise ratio does not meet the defined threshold, the ventilator selects to perform operations 1004, 1006, 1008, 1010, and 1012 for the next received sensor measurement from operation 1002.

During difference operation 1014, the ventilator determines or calculates a difference between the residual base and a residual value of a most recently received sensor measurement taken after the residual base was found.

During the trigger threshold decision operation 1016, the ventilator determines if a trigger sensitivity has been met based on a comparison of the difference to a trigger sensitivity. At trigger threshold decision operation 1016, the ventilator compares the difference to a trigger sensitivity. If the ventilator determines during operation 1016 that the difference meets the trigger sensitivity, the ventilator determines a first result. In response to the first result determination during trigger threshold decision operation 1016 the ventilator selects to perform inspiration operation 1018. If the ventilator determines during operation 1016 that the difference does not meet the trigger sensitivity, the ventilator determines a second results based on the comparison. In response to the second result determination during trigger threshold decision operation 1016 the ventilator selects to perform time operation 1020 or to perform difference operation 1014 again based on the next most recently received sensor measurement.

At inspiration operation 1018, the ventilator triggers inspiration. The triggering of inspiration ends the exhalation. During inspiration, the ventilator delivers breathing gas to the patient. In some aspects, the ventilator delivers breathing gas to the patient according a set breath type during inspiration.

As discussed above, in some aspects, method 1000 includes an optional time operation 1020. At time operation 1020, the ventilator determines if an apnea time period has been met or in other words if exhalation has been going on for too long. If the ventilator determines that the apnea time period has been met during time operation 1020, the ventilator performs inspiration operation 1018. If the ventilator determines that the apnea time period has not been met during time operation 1020, the ventilator continues to perform decision operation 1016.

Those skilled in the art will recognize that the methods and systems of the present disclosure may be implemented in many manners and as such are not to be limited by the foregoing exemplary aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for triggering inhalation during spontaneous or assisted ventilation of a patient on a mechanical ventilator, comprising:
    monitoring, during an exhalation phase, a physiologic parameter signal of a patient receiving ventilation on a mechanical ventilator;
    tracking a distortion indicator in the physiologic parameter signal, wherein the distortion indicator comprises a deviation of a residual value of the physiologic parameter signal from a residual base;
    applying a sensitivity check to the distortion indicator;
    detecting a patient inhalation effort in response to the sensitivity check; and
    triggering an inhalation by the mechanical ventilator in response to the detected patient inhalation effort.

2. The method of claim 1, wherein applying the sensitivity check comprises comparing the distortion indicator to a sensitivity threshold.

3. The method of claim 1, further comprising receiving measurements of a physiologic parameter from one or more sensors coupled to the ventilator, the measurements forming the physiologic parameter signal.

4. The method of claim 3, wherein the physiologic parameter comprises flow or pressure.

5. The method of claim 3, wherein the one or more sensors are non-invasive.

6. The method of claim 1, further comprising, after applying the sensitivity check, setting a flag indicating a presence of the detected patient inhalation effort.

7. The method of claim 1, further comprising displaying the distortion indicator versus time on a graph with a pressure or flow waveform.

8. The method of claim 1, wherein the residual value and residual base are dynamically updated during exhalation.

9. The method of claim 1, wherein detecting the patient inhalation effort occurs before an exhalation flow or pressure has crossed a trigger baseline.

10. The method of claim 1, further comprising:
    further monitoring the physiologic parameter signal during an inhalation phase;
    applying a second sensitivity check to the distortion indicator;
    detecting a patient exhalation effort in response to the second sensitivity check; and
    cycling the mechanical ventilator to exhalation in response to the detected patient exhalation effort.

11. The method of claim 1, wherein the residual value is a difference between a current value of the physiologic parameter signal and an averaged value of a defined number of recent values of the physiologic parameter signal.

12. The method of claim 1, wherein the residual base is equal to a prior residual value.

13. A method for triggering inhalation during spontaneous or assisted ventilation of a patient on a mechanical ventilator, comprising:
    monitoring, during an exhalation phase, a flow or pressure signal of a patient receiving ventilation on a mechanical ventilator;
    tracking a distortion indicator in the flow or pressure signal, wherein the distortion indicator comprises a deviation of a residual value of the flow or pressure signal from a residual base;
    dynamically updating the distortion indicator during the exhalation phase;

detecting, from the distortion indicator, an occurrence of a distortion indicative of an inhalation effort before the flow or pressure signal has crossed a trigger baseline; and triggering an inhalation by the mechanical ventilator as a result of the detected occurrence of the distortion.

14. The method of claim 13, further comprising displaying the distortion indicator on a display screen of the mechanical ventilator.

15. The method of claim 13, wherein the residual value is a difference between a current value of the flow or pressure signal and an averaged value of a defined number of recent values of the flow or pressure signal.

16. The method of claim 13, wherein the residual base is equal to a prior residual value.

17. A method for triggering inspiration during spontaneous or assisted ventilation of a patient on a ventilator, comprising:

monitoring, from one or more non-invasive sensors during exhalation, a physiological parameter signal of a patient receiving ventilation from a ventilator;

determining, by a microprocessor, a first residual value and a signal-to-noise ratio of the physiological parameter signal;

determining, by the microprocessor, that the signal-to-noise ratio exceeds a noise threshold;

based on the signal-to-noise ratio exceeding the noise threshold, setting, by the microprocessor, a residual base equal to the first residual value;

determining, by the microprocessor, a second residual value of the physiological parameter signal;

determining, by the microprocessor, that a deviation between the second residual value and the residual base satisfies a trigger condition;

detecting, in response to the satisfied trigger condition, a patient effort to inhale; and triggering inspiration in response to the detection of the patient effort.

18. The method of claim 17, wherein the trigger condition comprises a sensitivity threshold.

19. The method of claim 17, wherein the first residual value and the second residual value occur within an exhalation phase of a breath.

* * * * *